(12) United States Patent
Qing

(10) Patent No.: US 7,749,486 B2
(45) Date of Patent: Jul. 6, 2010

(54) TUMOR MODELS EMPLOYING GREEN FLUORESCENT PROTEIN

(75) Inventor: Weiguo Qing, Denville, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 108 days.

(21) Appl. No.: 11/728,403

(22) Filed: Mar. 26, 2007

(65) Prior Publication Data

US 2007/0231789 A1   Oct. 4, 2007

Related U.S. Application Data

(60) Provisional application No. 60/788,250, filed on Mar. 31, 2006.

(51) Int. Cl.
*A61K 49/00* (2006.01)
*A61B 5/00* (2006.01)

(52) U.S. Cl. .......................... 424/9.2; 424/9.6; 436/64

(58) Field of Classification Search .................. None
See application file for complete search history.

(56) References Cited

U.S. PATENT DOCUMENTS

| 5,994,309 | A | * | 11/1999 | Mazar et al. | 514/16 |
| 6,232,107 | B1 | * | 5/2001 | Bryan et al. | 435/189 |
| 7,239,384 | B2 | * | 7/2007 | Kawano | 356/317 |
| 7,270,812 | B2 | * | 9/2007 | Shino et al. | 424/93.6 |

FOREIGN PATENT DOCUMENTS

| WO | WO 98/49336 | 11/1998 |
| WO | WO 98/49336 A1 | 11/1998 |
| WO | WO 00/40274 A1 | 7/2000 |
| WO | WO 01/05946 | 1/2001 |

OTHER PUBLICATIONS

Shoemaker et al., Proc. Am. Assoc. Cancer Research vol. 26, p. 330 (1985).
Nakanishi et al., Cancer Sci. vol. 94 pp. 112-118 (2003).
Fodstad, et al., Int. J. Cancer vol. 41 pp. 442-449 (1988).
Yang et al., Clin. Cancer Research vol. 5, pp. 3549-3559 (1999).
Wang et al., Int. J. Cancer. vol. 112, pp. 994-1002 (2004).
Thews Oliver, et al., International Journal of Oncology, vol. 27, No. 3, pp. 705-712 (2005), XP002430791.
Corti C et al *Jour. Of Cancer Research and Clin. Onc.*, 122(3), 1540160 (1996).
Katano M et al *Jour. Of Cancer Research and Clin. Onc.*, 108(2), 197-203 (1984).
Qing W, et al, *Proceedings of the American Assoc. for Cancer Res.* 47, p. 812 (206).
Thews, O. et al *International Jour. of Onc*, 27(3) 705-712 (2005).

* cited by examiner

*Primary Examiner*—Karen A Canella
(74) *Attorney, Agent, or Firm*—George W. Johnston; Patricia S. Rocha-Tramaloni; Kimberly J. Prior

(57) ABSTRACT

The present invention relates to a LOX-GFP marker and methods of analyzing tumor burden in ascites or in lung. The invention also relates to a new LOX-GFP-LM cell line which demonstrates increased lung metastasis. The methods of the invention result in better quantitative tumor burden assessment and improved efficacy evaluation. These improved models provide a feasible alternative for ascites or experimental metastasis evaluation of novel cancer therapeutics.

10 Claims, 39 Drawing Sheets

SC LOX

SC LOX-GFP

IV LOX-GFP-LM Lung Metastasis

FIGURE 2A

| Affy Probe ID | Gene Symbol | Description | LM vs LOX | Fold Change GFP vs LOX | LM vs GFP | P-value | Averages Parental | Averages GFP | Averages GFP-LM |
|---|---|---|---|---|---|---|---|---|---|
| 204614_at | SERPINB2 | serine (or cysteine) proteinase inhibitor, clade B (ovalbumin), member 2 | 4.93 | 0.37 | 13.31 | 2.21E-06 | 304 | 113 | 1500 |
| 226281_at | DNER | delta-notch-like EGF repeat-containing transmembrane | 3.95 | 0.31 | 12.65 | 9.43E-06 | 55 | 17 | 219 |
| 1554001_at | TRIM37 | tripartite motif-containing 37 | 10.72 | 0.97 | 11.04 | 1.28E-05 | 34 | 33 | 363 |
| 213725_x_at | LOC283824 | hypothetical protein LOC283824 | 8.45 | 0.82 | 10.27 | 2.86E-05 | 16 | 13 | 138 |
| 1556499_s_at | COL1A1 | collagen, type I, alpha 1 | 1.77 | 0.18 | 9.57 | 0.01875 | 349 | 64 | 616 |
| 213009_s_at | TRIM37 | tripartite motif-containing 37 | 19.12 | 2.22 | 8.60 | 3.99E-08 | 99 | 220 | 1892 |
| 210095_s_at | IGFBP3 | insulin-like growth factor binding protein 3 | 3.23 | 0.40 | 8.13 | 2.00E-05 | 273 | 108 | 881 |
| 212143_s_at | IGFBP3 | insulin-like growth factor binding protein 3 | 2.27 | 0.30 | 7.44 | 4.94E-08 | 103 | 31 | 234 |
| 222486_s_at | ADAMTS1 | a disintegrin-like and metalloprotease (reprolysin type) with thrombospondin type 1 motif, 1 | 4.57 | 0.62 | 7.36 | 1.97E-08 | 46 | 29 | 210 |
| 222162_s_at | ADAMTS1 | a disintegrin-like and metalloprotease (reprolysin type) with thrombospondin type 1 motif, 1 | 3.13 | 0.43 | 7.19 | 5.34E-07 | 354 | 154 | 1106 |

FIGURE 2B

| Affy Probe ID | Gene Symbol | Description | LM vs LOX | Fold Change GFP vs LOX | LM vs GFP | P-value | Averages Parental | GFP | GFP-LM |
|---|---|---|---|---|---|---|---|---|---|
| 231518_at | LOC283867 | hypothetical protein LOC283867 | 7.43 | 1.08 | 6.85 | 1.13E-08 | 22 | 24 | 164 |
| 224941_at | PAPPA | pregnancy-associated plasma protein A, pappalysin 1 | 1.43 | 0.23 | 6.33 | 0.00086 | 104 | 24 | 149 |
| 206343_s_at | NRG1 | neuregulin 1 | 2.54 | 0.41 | 6.28 | 1.44E-06 | 552 | 224 | 1404 |
| 231766_s_at | COL12A1 | collagen, type XII, alpha 1 | 3.62 | 0.59 | 6.18 | 0.00015 | 22 | 13 | 81 |
| 226991_at | NFATC2 | Nuclear factor of activated T-cells, cytoplasmic, calcineurin-dependent 2 | 4.76 | 0.86 | 5.56 | 3.77E-06 | 84 | 72 | 398 |
| 224940_s_at | PAPPA | pregnancy-associated plasma protein A, pappalysin 1 | 1.95 | 0.36 | 5.42 | 0.004285996 | 90 | 32 | 176 |
| 211506_s_at | IL8 | interleukin 8 | 2.62 | 0.49 | 5.38 | 0.000557857 | 451 | 220 | 1182 |
| 1569727_at | --- | Homo sapiens, Similar to hypothetical gene LOC130797, clone IMAGE:5395354, Mrna | 4.05 | 0.77 | 5.27 | 2.92E-06 | 14 | 11 | 59 |
| 228442_at | NFATC2 | Nuclear factor of activated T-cells, cytoplasmic, calcineurin-dependent 2 | 3.48 | 0.68 | 5.15 | 1.56E-05 | 75 | 51 | 263 |

FIGURE 2C

| Affy Probe ID | Gene Symbol | Description | Fold Change LM vs LOX | Fold Change GFP vs LOX | LM vs GFP | P-value | Averages Parental | Averages GFP | Averages GFP-LM |
|---|---|---|---|---|---|---|---|---|---|
| 202729_s_at | LTBP1 | latent transforming growth factor beta binding protein 1 | 3.51 | 0.68 | 5.13 | 1.03E-05 | 19 | 13 | 67 |
| 201506_at | TGFBI | transforming growth factor, beta-induced, 68kDa | 6.31 | 1.23 | 5.11 | 2.58E-08 | 878 | 1083 | 5540 |
| 202310_s_at | COL1A1 | collagen, type I, alpha 1 | 1.01 | 0.20 | 5.05 | 0.00249 | 78 | 16 | 79 |
| 228128_x_at | PAPPA | pregnancy-associated plasma protein A, pappalysin 1 | 1.49 | 0.30 | 4.99 | 0.013393085 | 111 | 33 | 165 |
| 230746_at | STC1 | Stanniocalcin 1 | 2.62 | 0.53 | 4.92 | 0.00019 | 75 | 40 | 196 |
| 231947_at | MYCT1 | myc target 1 | 4.38 | 0.92 | 4.77 | 3.41E-07 | 20 | 19 | 89 |
| 201438_at | COL6A3 | collagen, type VI, alpha 3 | 1.77 | 0.38 | 4.68 | 0.00104 | 70 | 26 | 124 |
| 226695_at | PRRX1 | paired related homeobox 1 | 1.61 | 0.35 | 4.61 | 0.015356564 | 111 | 39 | 179 |
| 242005_at | --- | --- | 4.41 | 0.96 | 4.61 | 0.00 | 13 | 12 | 57 |
| 225512_at | ZBTB38 | zinc finger and BTB domain containing 38 | 4.32 | 0.94 | 4.60 | 0.00 | 200 | 187 | 863 |
| 201170_s_at | BHLHB2 | basic helix-loop-helix domain containing, class B, 2 | 3.81 | 0.84 | 4.53 | 0.00 | 63 | 53 | 240 |
| 205476_at | CCL20 | chemokine (C-C motif) ligand 20 | 2.98 | 0.67 | 4.45 | 0.00 | 594 | 399 | 1773 |
| 204597_x_at | STC1 | stanniocalcin 1 | 3.64 | 0.84 | 4.33 | 0.00 | 36 | 30 | 132 |
| 211026_s_at | MGLL | monoglyceride lipase /// monoglyceride lipase | 2.43 | 0.57 | 4.30 | 0.00 | 77 | 44 | 188 |

FIGURE 2D

| Affy Probe ID | Gene Symbol | Description | LM vs LOX | Fold Change GFP vs LOX | LM vs GFP | P-value | Averages Parental | Averages GFP | Averages GFP-LM |
|---|---|---|---|---|---|---|---|---|---|
| 218980_at | FHOD3 | formin homology 2 domain containing 3 | 2.61 | 0.62 | 4.23 | 0.00 | 28 | 17 | 73 |
| 203504_s_at | ABCA1 | ATP-binding cassette, sub-family A (ABC1), member 1 | 1.91 | 0.46 | 4.15 | 0.00 | 54 | 25 | 103 |
| 210592_s_at | SAT | spermidine/spermine N1-acetyltransferase | 2.85 | 0.69 | 4.11 | 0.00 | 51 | 35 | 146 |
| 225664_at | COL12A1 | collagen, type XII, alpha 1 | 3.44 | 0.84 | 4.09 | 0.00 | 173 | 145 | 595 |
| 203455_s_at | SAT | spermidine/spermine N1-acetyltransferase | 3.24 | 0.83 | 3.88 | 0.00 | 51 | 42 | 164 |
| 221478_at | BNIP3L | BCL2/adenovirus E1B 19kDa interacting protein 3-like /// BCL2/adenovirus E1B 19kDa interacting protein 3-like | 3.26 | 0.86 | 3.80 | 0.00 | 75 | 65 | 246 |
| 1564008_at | COL27A1 | Collagen, type XXVII, alpha 1 | 3.96 | 1.06 | 3.73 | 0.00 | 39 | 41 | 154 |
| 217853_at | TENS1 | tensin-like SH2 domain containing 1 | 1.57 | 0.42 | 3.72 | 0.03 | 67 | 28 | 106 |
| 231879_at | COL12A1 | collagen, type XII, alpha 1 | 2.69 | 0.72 | 3.72 | 0.00 | 28 | 20 | 76 |
| 200878_at | EPAS1 | endothelial PAS domain protein 1 | 1.92 | 0.52 | 3.71 | 0.00 | 54 | 28 | 104 |
| 232027_at | SYNE1 | spectrin repeat containing, nuclear envelope 1 | 4.65 | 1.28 | 3.63 | 0.00 | 95 | 122 | 442 |

FIGURE 2E

| Affy Probe ID | Gene Symbol | Description | LM vs LOX | Fold Change GFP vs LOX | LM vs GFP | P-value | Averages Parental | GFP | GFP-LM |
|---|---|---|---|---|---|---|---|---|---|
| 203505_at | ABCA1 | ATP-binding cassette, sub-family A (ABC1), member 1 | 1.47 | 0.42 | 3.51 | 0.00 | 136 | 57 | 200 |
| 204797_s_at | EML1 | echinoderm microtubule associated protein like 1 | 3.06 | 0.88 | 3.49 | 0.00 | 32 | 28 | 97 |
| 204595_s_at | STC1 | stanniocalcin 1 | 4.51 | 1.30 | 3.46 | 0.00 | 56 | 73 | 252 |
| 241994_at | XDH | Xanthine dehydrogenase | 2.68 | 0.78 | 3.44 | 0.00 | 19 | 15 | 50 |
| 205990_s_at | WNT5A | wingless-type MMTV integration site family, member 5A | 2.00 | 0.58 | 3.43 | 0.00 | 666 | 388 | 1334 |
| 226844_at | MOBKL2B | MOB1, Mps One Binder kinase activator-like 2B (yeast) | 2.43 | 0.71 | 3.42 | 0.00 | 306 | 217 | 743 |
| 227061_at | --- | CDNA FLJ44429 fis, clone UTERU2015653 | 3.99 | 1.17 | 3.41 | 0.00 | 41 | 48 | 165 |
| 208483_x_at | KRTHA3A | keratin, hair, acidic, 3A | 2.27 | 0.67 | 3.38 | 0.00 | 325 | 219 | 739 |
| 213256_at | 38414 | membrane-associated ring finger (C3HC4) 3 | 3.56 | 1.05 | 3.38 | 0.00 | 15 | 15 | 52 |
| 205067_at | IL1B | interleukin 1, beta | 4.16 | 1.23 | 3.38 | 0.00 | 1496 | 1841 | 6216 |
| 1552485_at | LACTB | lactamase, beta | 3.09 | 0.92 | 3.37 | 0.00 | 37 | 34 | 115 |
| 229568_at | MOBKL2B | MOB1, Mps One Binder kinase activator-like 2B (yeast) | 4.03 | 1.20 | 3.36 | 0.00 | 73 | 87 | 292 |

FIGURE 2F

| Affy Probe ID | Gene Symbol | Description | LM vs LOX | Fold Change GFP vs LOX | LM vs GFP | P-value | Averages Parental | Averages GFP | Averages GFP-LM |
|---|---|---|---|---|---|---|---|---|---|
| 224942_at | PAPPA | pregnancy-associated plasma protein A, pappalysin 1 | 1.74 | 0.52 | 3.31 | 0.00 | 36 | 19 | 63 |
| 237411_at | ADAMTS6 | a disintegrin-like and metalloprotease (reprolysin type) with thrombospondin type 1 motif, 6 | 3.12 | 0.95 | 3.28 | 9.60E-05 | 316 | 301 | 986 |
| 231227_at | WNT5A | Wingless-type MMTV integration site family, member 5A | 2.15 | 0.66 | 3.27 | 0.005257199 | 166 | 109 | 357 |
| 225102_at | MGLL | monoglyceride lipase | 2.79 | 0.86 | 3.26 | 3.80E-05 | 73 | 62 | 203 |
| 204472_at | GEM | GTP binding protein overexpressed in skeletal muscle | 3.33 | 1.03 | 3.24 | 0.000271689 | 80 | 82 | 267 |
| 204596_s_at | STC1 | stanniocalcin 1 | 2.78 | 0.86 | 3.24 | 2.74E-05 | 31 | 27 | 86 |
| 1555259_at | ZAK | Sterile alpha motif and leucine zipper containing kinase AZK | 2.96 | 0.92 | 3.21 | 0.000256217 | 95 | 88 | 281 |
| 39402_at | IL1B | interleukin 1, beta | 3.02 | 0.95 | 3.20 | 2.33E-05 | 1355 | 1280 | 4096 |
| 209098_s_at | JAG1 | jagged 1 (Alagille syndrome) | 3.16 | 0.99 | 3.18 | 7.36E-05 | 24 | 24 | 76 |
| 232080_at | HECW2 | HECT, C2 and WW domain containing E3 ubiquitin protein ligase 2 | 3.28 | 1.07 | 3.08 | 0.000105271 | 31 | 33 | 101 |

FIGURE 2G

| Affy Probe ID | Gene Symbol | Description | Fold Change LM vs LOX | Fold Change GFP vs LOX | LM vs GFP | P-value | Averages Parental | Averages GFP | Averages GFP-LM |
|---|---|---|---|---|---|---|---|---|---|
| 205932_s_at | MSX1 | msh homeo box homolog 1 (Drosophila) | 0.69 | 2.07 | -3.02 | 3.09E-06 | 24 | 50 | 16 |
| 241763_s_at | --- | --- | 0.63 | 1.90 | -3.02 | 0.002894049 | 47 | 89 | 29 |
| 202856_s_at | SLC16A3 | solute carrier family 16 (monocarboxylic acid transporters), member 3 | 0.41 | 1.24 | -3.02 | 0.038738223 | 71 | 88 | 29 |
| 223243_s_at | C1orf22 | chromosome 1 open reading frame 22 | 0.51 | 1.57 | -3.06 | 0.000873698 | 89 | 139 | 46 |
| 226611_s_at | PRR6 | proline rich 6 | 0.36 | 1.12 | -3.06 | 2.43E-05 | 37 | 41 | 13 |
| 204388_s_at | MAOA | monoamine oxidase A | 0.67 | 2.07 | -3.07 | 8.64E-05 | 42 | 86 | 28 |
| 213135_at | TIAM1 | T-cell lymphoma invasion and metastasis 1 | 0.45 | 1.38 | -3.08 | 0.000115042 | 23 | 31 | 10 |
| 203939_at | NT5E | 5'-nucleotidase, ecto (CD73) | 0.80 | 2.47 | -3.09 | 0.000507456 | 320 | 789 | 255 |
| 209406_at | BAG2 | BCL2-associated athanogene 2 | 0.57 | 1.78 | -3.14 | 0.003301833 | 45 | 79 | 25 |
| 201730_s_at | TPR | translocated promoter region (to activated MET oncogene) | 0.79 | 2.49 | -3.16 | 0.001806326 | 209 | 520 | 165 |
| 1553972_a_at | CBS | cystathionine-beta-synthase | 0.52 | 1.65 | -3.18 | 5.34E-06 | 31 | 51 | 16 |
| 224443_at | MGC14801 | hypothetical protein MGC14801 /// hypothetical protein MGC14801 | 0.35 | 1.12 | -3.18 | 2.16E-05 | 40 | 45 | 14 |
| 212741_at | MAOA | monoamine oxidase A | 0.64 | 2.08 | -3.23 | 2.33E-05 | 55 | 115 | 36 |

FIGURE 2H

| Affy Probe ID | Gene Symbol | Description | LM vs LOX | Fold Change GFP vs LOX | LM vs GFP | P-value | Averages Parental | GFP | GFP-LM |
|---|---|---|---|---|---|---|---|---|---|
| 219215_s_at | SLC39A4 | solute carrier family 39 (zinc transporter), member 4 | 0.31 | 1.00 | -3.24 | 5.61E-06 | 143 | 143 | 44 |
| 225051_at | EPB41 | erythrocyte membrane protein band 4.1 (elliptocytosis 1, RH-linked) | 0.48 | 1.59 | -3.28 | 0.004195323 | 39 | 62 | 19 |
| 225407_at | MBP | Myelin basic protein | 0.30 | 0.97 | -3.28 | 1.18E-06 | 115 | 112 | 34 |
| 1557227_s_at | TPR | translocated promoter region (to activated MET oncogene) | 0.62 | 2.04 | -3.29 | 7.98E-05 | 21 | 43 | 13 |
| 212188_at | KCTD12 | potassium channel tetramerisation domain containing 12 /// potassium channel tetramerisation domain containing 12 | 0.76 | 2.52 | -3.32 | 0.002225727 | 210 | 531 | 160 |
| 202897_at | PTPNS1 | protein tyrosine phosphatase, non-receptor type substrate 1 | 0.41 | 1.36 | -3.36 | 0.001316867 | 42 | 57 | 17 |
| 226997_at | --- | cDNA FLJ10196 fis, clone HEMBA1004776 | 0.62 | 2.10 | -3.37 | 6.89E-06 | 23 | 48 | 14 |
| 204197_s_at | RUNX3 | runt-related transcription factor 3 | 0.35 | 1.21 | -3.41 | 8.55E-05 | 40 | 48 | 14 |

FIGURE 2I

| Affy Probe ID | Gene Symbol | Description | Fold Change LM vs LOX | Fold Change GFP vs LOX | LM vs GFP | P-value | Averages Parental | Averages GFP | Averages GFP-LM |
|---|---|---|---|---|---|---|---|---|---|
| 226194_at | C13orf8 | chromosome 13 open reading frame 8 | 0.33 | 1.17 | -3.54 | 7.94E-06 | 139 | 163 | 46 |
| 205080_at | RARB | retinoic acid receptor, beta | 0.38 | 1.35 | -3.54 | 0.002665862 | 62 | 84 | 24 |
| 226610_at | PRR6 | proline rich 6 | 0.38 | 1.37 | -3.63 | 4.67E-05 | 31 | 43 | 12 |
| 206958_s_at | UPF3A | UPF3 regulator of nonsense transcripts homolog A (yeast) | 0.42 | 1.55 | -3.68 | 0.003233044 | 88 | 137 | 37 |
| 1555778_a_at | POSTN | periostin, osteoblast specific factor | 0.18 | 0.68 | -3.69 | 0.000451816 | 61 | 41 | 11 |
| 227407_at | FLJ90013 | hypothetical protein FLJ90013 | 0.42 | 1.55 | -3.70 | 3.94E-05 | 28 | 43 | 12 |
| 205458_at | MC1R | melanocortin 1 receptor (alpha melanocyte stimulating hormone receptor) | 0.23 | 0.84 | -3.70 | 0.000982791 | 137 | 116 | 31 |
| 203636_at | MID1 | midline 1 (Opitz/BBB syndrome) | 0.35 | 1.30 | -3.73 | 0.00083587 | 35 | 45 | 12 |
| 205563_at | KISS1 | KiSS-1 metastasis-suppressor | 0.49 | 1.95 | -3.96 | 1.52E-05 | 57 | 112 | 28 |
| 204198_s_at | RUNX3 | runt-related transcription factor 3 | 0.32 | 1.28 | -4.00 | 0.001227508 | 45 | 57 | 14 |

FIGURE 2J

| Affy Probe ID | Gene Symbol | Description | Fold Change | | | P-value | Averages | | |
|---|---|---|---|---|---|---|---|---|---|
| | | | LM vs LOX | GFP vs LOX | LM vs GFP | | Parental | GFP | GFP-LM |
| 218237_s_at | SLC38A1 | solute carrier family 38, member 1 | 0.54 | 2.15 | -4.00 | 1.97E-06 | 161 | 346 | 86 |
| 225273_at | KIAA1280 | KIAA1280 protein | 0.44 | 1.79 | -4.06 | 6.54E-07 | 34 | 60 | 15 |
| 203637_s_at | MID1 | midline 1 (Opitz/BBB syndrome) | 0.34 | 1.40 | -4.13 | 0.001577228 | 33 | 46 | 11 |
| 206995_x_at | SCARF1 | scavenger receptor class F, member 1 | 0.82 | 3.70 | -4.14 | 3.46E-05 | 11 | 41 | 9 |
| 212681_at | EPB41L3 | erythrocyte membrane protein band 4.1-like 3 | 0.73 | 5.23 | -4.22 | 0.00020868 | 8 | 42 | 6 |
| 223059_s_at | C10orf45 | chromosome 10 open reading frame 45 | 0.72 | 3.13 | -4.32 | 0.002255262 | 17 | 52 | 12 |
| 213332_at | PAPPA2 | Pappalysin 2 | 0.42 | 1.83 | -4.40 | 0.000200075 | 35 | 64 | 15 |
| 223058_at | C10orf45 | chromosome 10 open reading frame 45 | 0.56 | 2.48 | -4.41 | 0.000158117 | 24 | 60 | 14 |
| 204726_at | CDH13 | cadherin 13, H-cadherin (heart) | 0.38 | 2.26 | -4.62 | 0.000401679 | 20 | 46 | 8 |
| 225688_s_at | PHLDB2 | pleckstrin homology-like domain, family B, member 2 | 0.52 | 2.40 | -4.64 | 2.40E-05 | 217 | 523 | 113 |
| 225803_at | FBXO32 | F-box protein 32 | 0.27 | 1.30 | -4.76 | 2.27E-06 | 105 | 137 | 29 |

FIGURE 2K

| Affy Probe ID | Gene Symbol | Description | Fold Change | | | P-value | Averages | | |
|---|---|---|---|---|---|---|---|---|---|
| | | | LM vs LOX | GFP vs LOX | LM vs GFP | | Parental | GFP | GFP-LM |
| 226517_at | BCAT1 | branched chain aminotransferase 1, cytosolic | 0.10 | 0.66 | -4.76 | 0.009711968 | 72 | 48 | 7 |
| 225285_at | BCAT1 | branched chain aminotransferase 1, cytosolic | 0.09 | 0.53 | -5.58 | 0.01784924 | 147 | 78 | 14 |
| 225328_at | FBXO32 | F-box protein 32 | 0.34 | 2.08 | -6.20 | 0.000382801 | 41 | 85 | 14 |
| 206710_s_at | EPB41L3 | erythrocyte membrane protein band 4.1-like 3 | 0.73 | 6.84 | -6.27 | 2.37E-05 | 9 | 63 | 7 |
| 210136_at | MBP | Myelin basic protein | 0.23 | 1.45 | -6.37 | 0.002284996 | 115 | 166 | 26 |
| 211776_s_at | EPB41L3 | erythrocyte membrane protein band 4.1-like 3 /// erythrocyte membrane protein band 4.1-like 3 | 0.90 | 6.11 | -6.79 | 2.77E-05 | 16 | 99 | 15 |
| 203936_s_at | MMP9 | matrix metalloproteinase 9 (gelatinase B, 92kDa gelatinase, 92kDa type IV collagenase) | 0.25 | 1.68 | -6.82 | 0.001260637 | 214 | 359 | 53 |

FIGURE 2L

| Affy Probe ID | Gene Symbol | Description | LM vs LOX | Fold Change GFP vs LOX | LM vs GFP | P-value | Averages Parental | Averages GFP | Averages GFP-LM |
|---|---|---|---|---|---|---|---|---|---|
| 222108_at | AMIGO2 | amphoterin induced gene 2 | 0.15 | 1.47 | -9.74 | 0.000165723 | 230 | 339 | 35 |
| 207663_x_at | GAGE3 | G antigen 3 | 0.90 | 18.99 | -18.21 | 5.07E-06 | 10 | 182 | 9 |
| 200953_s_at | CCND2 | cyclin D2 | 0.44 | 10.27 | -18.41 | 1.43E-06 | 18 | 184 | 8 |
| 208235_x_at | GAGE5 /// GAGE7 /// GAGE7B | G antigen 5 /// G antigen 7 /// G antigen 7B | 0.97 | 59.67 | -51.66 | 7.46E-08 | 9 | 517 | 8 |
| 207086_x_at | GAGE2 /// GAGE4 /// GAGE5 /// GAGE6 /// GAGE7 /// GAGE7B /// GAGE8 | G antigen 2 /// G antigen 4 /// G antigen 5 /// G antigen 6 /// G antigen 7 /// G antigen 7B /// G antigen 8 | 1.01 | 68.25 | -63.62 | 1.93E-10 | 9 | 636 | 9 |
| 208155_x_at | GAGE4 /// GAGE5 /// GAGE6 /// GAGE7B | G antigen 4 /// G antigen 5 /// G antigen 6 /// G antigen 7B | 0.93 | 73.92 | -63.90 | 1.44E-07 | 9 | 639 | 8 |
| 206640_x_at | GAGE2 /// GAGE4 /// GAGE5 /// GAGE6 /// GAGE7 /// GAGE7B | G antigen 2 /// G antigen 4 /// G antigen 5 /// G antigen 6 /// G antigen 7 /// G antigen 7B | 0.94 | 71.58 | -68.97 | 9.17E-08 | 10 | 690 | 9 |

FIGURE 2M

| Affy Probe ID | Gene Symbol | Description | Fold Change | | | P-value | Averages | | |
|---|---|---|---|---|---|---|---|---|---|
| | | | LM vs LOX | GFP vs LOX | LM vs GFP | | Parental | GFP | GFP-LM |
| 207739_s_at | GAGE1 /// GAGE2 /// GAGE3 /// GAGE4 /// GAGE5 /// GAGE6 /// GAGE7 /// GAGE7B /// GAGE8 | G antigen 1 /// G antigen 2 /// G antigen 3 /// G antigen 4 /// G antigen 5 /// G antigen 6 /// G antigen 7 /// G antigen 7B /// G antigen 8 | 0.84 | 61.71 | -69.12 | 1.26E-07 | 11 | 691 | 9 |
| 1557060_at | LOC148756 | hypothetical protein LOC148756 | 0.02 | 1.47 | -70.86 | 0.018100783 | 481 | 709 | 8 |

FIGURE 3

| | Mouse 1 (RFU) | Mouse 2 (RFU) | Group Mean (RFU) | % of Control (Vehicle) |
|---|---|---|---|---|
| Vehicle for Taxol | 46668808 | 38830596 | 42749702 | 100 |
| Taxol 10 mg/kg iv, 0.2 ml, 3 doses | 4180371 | 1115161 | 2647766 | 6 |
| Taxol 10 mg/kg iv, 0.2 ml, 2 doses | 1726088 | 932263 | 1329175.5 | 3 |
| Taxol 10 mg/kg iv, 0.2 ml, single dose | 23026688 | 76128688 | 49577688 | 116 |
| Vehicle for Compound A | 57993 | 40375192 | 20216592.5 | 100 |
| Compound A 40 mg/kg po, 0.2 ml, 3 doses | 720547 | 279651 | 500099 | 2 |
| Compound A 40 mg/kg po, 0.2 ml, 2 doses | 11321294 | 1078210 | 6199752 | 31 |
| Compound A 40 mg/kg po, 0.2 ml, single dose | 6860373 | 49589592 | 28224982.5 | 140 |

FIGURE 4

| | Mouse 1 (RFU) | Mouse 2 (RFU) | Mouse 3 (RFU) | Mouse 4 (RFU) | Mouse 5 (RFU) | Group Mean (RFU) | % of Control (Vehicle) |
|---|---|---|---|---|---|---|---|
| Vehicle for Compound C | 102198 | 61935 | 8314959 | 47587963 | 29468175 | 1.71E+07 | 100 |
| Compound C 40 mg/kg sc, 0.2 ml, 6 doses | 14584285 | 120970 | 8221417 | 14723969 | 18859131 | 1.13E+07 | 66 |
| Vehicle for Compound B | 48995131 | 39816203 | 69380967 | 40050403 | 26161507 | 4.50E+07 | 100 |
| Compound B 200 mg po bid 0.2ml, 12 doses | | 2448626 | 719126 | 658675 | 311694 | 1.03E+06 | 2 |
| Vehicle for Taxol | 32218941 | 37279679 | | 3484173 | 5489785 | 1.96E+07 | 100 |
| Taxol 15 mg/kg iv, 0.2 ml, 3 doses | | 5220027 | 9186100 | 978809 | 2861760 | 4.56E+06 | 24 |

FIGURE 5

| | Mouse 1 (RFU) | Mouse 2 (RFU) | Mouse 3 (RFU) | Mouse 4 (RFU) | Group Mean (RFU) | % of Control (Vehicle) |
|---|---|---|---|---|---|---|
| Vehicle for Compound D | 1914478 | 11606322 | 25495806 | 29654428 | 17167759 | 100 |
| Compound D 100 mg/kg po bid, 0.2 ml, 6 doses | 396751 | 1652077 | 564693 | 2079222 | 1173186 | 7 |
| Compound D 50 mg/kg po bid, 0.2 ml, 6 doses | 14068767 | 495815 | 9494386 | 339706 | 6099669 | 36 |
| Compound D 25 mg/kg po bid, 0.2 ml, 6 doses | 2713930 | 2679062 | 4137508 | 5858146 | 3847162 | 22 |
| Taxol 15 mg/kg iv, 0.2 ml, 2 doses | 59141 | 94893 | 3614922 | 99922 | 967219 | 6 |
| Taxol 15 mg/kg iv, 0.2 ml, 2 doses + Compound D 100 mg/kg po bid, 0.2 ml, 6 doses | 2063438 | 357122 | 125436 | 378335 | 731083 | 4 |
| Taxol 15 mg/kg iv, 0.2 ml, 2 doses + Compound D 50 mg/kg po bid, 0.2 ml, 6 doses | 1691195 | 1666794 | 126275 | 206520 | 987696 | 6 |
| Taxol 15 mg/kg iv, 0.2 ml, 2 doses + Compound D 25 mg/kg po bid, 0.2 ml, 6 doses | 85918 | 140979 | 10059 | 2993744 | 807675 | 5 |

FIGURE 16A
Restriction map for the GFP Expression vector:

The sequence starts with the CMV-promoter (nucleotide positions 1-600). The GFP ORF is situated between positions 670-1395, flanked by SfiI sites. The NotI-AscI linker is situated at position 1400-1410, followed by the IRES-NEO-module. The BstBI site is located at pos 2910, followed by the HSV-TK poly A site.

```
        ATGCATTAGTTATTAATAGTAATCAATTACGGGGTCATTAGTTCATAGCCCATATATGGA
                 10        20        30        40        50        60
        ----:----|----:----|----:----|----:----|----:----|----:----|
        TACGTAATCAATAATTATCATTAGTTAATGCCCCAGTAATCAAGTATCGGGTATATACCT

GTTCCGCGTTACATAACTTACGGTAAATGGCCCGCCTGGCTGACCGCCCAACGACCCCCG
                 70        80        90       100       110       120
        ----:----|----:----|----:----|----:----|----:----|----:----|
        CAAGGCGCAATGTATTGAATGCCATTTACCGGGCGGACCGACTGGCGGGTTGCTGGGGGC

CCCATTGACGTCAATAATGACGTATGTTCCCATAGTAACGCCAATAGGGACTTTCCATTG
                130       140       150       160       170       180
        ----:----|----:----|----:----|----:----|----:----|----:----|
        GGGTAACTGCAGTTATTACTGCATACAAGGGTATCATTGCGGTTATCCCTGAAAGGTAAC

ACGTCAATGGGTGGAGTATTTACGGTAAACTGCCCACTTGGCAGTACATCAAGTGTATCA
                190       200       210       220       230       240
        ----:----|----:----|----:----|----:----|----:----|----:----|
        TGCAGTTACCCACCTCATAAATGCCATTTGACGGGTGAACCGTCATGTAGTTCACATAGT

TATGCCAAGTACGCCCCCTATTGACGTCAATGACGGTAAATGGCCCGCCTGGCATTATGC
                250       260       270       280       290       300
        ----:----|----:----|----:----|----:----|----:----|----:----|
        ATACGGTTCATGCGGGGGATAACTGCAGTTACTGCCATTTACCGGGCGGACCGTAATACG

CCAGTACATGACCTTATGGGACTTTCCTACTTGGCAGTACATCTACGTATTAGTCATCGC
                310       320       330       340       350       360
        ----:----|----:----|----:----|----:----|----:----|----:----|
        GGTCATGTACTGGAATACCCTGAAAGGATGAACCGTCATGTAGATGCATAATCAGTAGCG

TATTACCATGGTGATGCGGTTTTGGCAGTACATCAATGGGCGTGGATAGCGGTTTGACTC
                370       380       390       400       410       420
        ----:----|----:----|----:----|----:----|----:----|----:----|
        ATAATGGTACCACTACGCCAAAACCGTCATGTAGTTACCCGCACCTATCGCCAAACTGAG
```

FIGURE 16B
Restriction map for the GFP Expression vector:

```
ACGGGGATTTCCAAGTCTCCACCCCATTGACGTCAATGGGAGTTTGTTTTGGCACCAAAA
         430       440       450       460       470       480
----:----|----:----|----:----|----:----|----:----|----:----|
TGCCCCTAAAGGTTCAGAGGTGGGGTAACTGCAGTTACCCTCAAACAAAACCGTGGTTTT

TCAACGGGACTTTCCAAAATGTCGTAACAACTCCGCCCCATTGACGCAAATGGGCGGTAG
         490       500       510       520       530       540
----:----|----:----|----:----|----:----|----:----|----:----|
AGTTGCCCTGAAAGGTTTTACAGCATTGTTGAGGCGGGGTAACTGCGTTTACCCGCCATC

GCGTGTACGGTGGGAGGTCTATATAAGCAGAGCTGGTTTAGTGAACCGTCAGATCCGCTA
         550       560       570       580       590       600
----:----|----:----|----:----|----:----|----:----|----:----|
CGCACATGCCACCCTCCAGATATATTCGTCTCGACCAAATCACTTGGCAGTCTAGGCGAT

GCGATTACGCCAAGCTCGAAATTAACCCTCACTAAAGGGAACAAAAGCTGGAGCTCCACa
         610       620       630       640       650       660
----:----|----:----|----:----|----:----|----:----|----:----|
CGCTAATGCGGTTCGAGCTTTAATTGGGAGTGATTTCCCTTGTTTTCGACCTCGAGGTGt

SfiI
             \
tcggccattATggccGAGCAAGCAGATCCTGAAGAACACCTGCCTGCAGGAGGTGATGAG
         670       680       690       700       710       720
----:----|----:----|----:----|----:----|----:----|----:----|
agccggtaaTAccggCTCGTTCGTCTAGGACTTCTTGTGGACGGACGTCCTCCACTACTC
       /
     SfiI CTACAAGGTGAACCTGGAGGGCATCGTTAACAACCACGTGTTCACCATGGAGGGCTGCGG
         730       740       750       760       770       780
----:----|----:----|----:----|----:----|----:----|----:----|
GATGTTCCACTTGGACCTCCCGTAGCAATTGTTGGTGCACAAGTGGTACCTCCCGACGCC CAAGGGCAACATCCTGTTCGGCAACCAATTGGTGCAGATCCGCGTGACCAAGGGCGCCCC
         790       800       810       820       830       840
----:----|----:----|----:----|----:----|----:----|----:----|
GTTCCCGTTGTAGGACAAGCCGTTGGTTAACCACGTCTAGGCGCACTGGTTCCCGCGGGG CCTGCCCTTCGCCTTCGACATCGTGAGCCCCGCCTTCCAGTACGGCAACCGTACGTTCAC
         850       860       870       880       890       900
----:----|----:----|----:----|----:----|----:----|----:----|
GGACGGGAAGCGGAAGCTGTAGCACTCGGGGCGGAAGGTCATGCCGTTGGCATGCAAGTG
```

FIGURE 16C
Restriction map for the GFP Expression vector:

```
CAAGTACCCCAACGACATCAGCGACTACTTCATCCAGAGCTTCCCCGCCGGCTTCATGTA
         910       920       930       940       950       960
----:----|----:----|----:----|----:----|----:----|----:----|
GTTCATGGGGTTGCTGTAGTCGCTGATGAAGTAGGTCTCGAAGGGGCGGCCGAAGTACAT

CGAGCGCACCCTGCGCTACGAGGACGGCGGCCTGGTGGAGATCCGCAGCGACATCAACCT
         970       980       990      1000      1010      1020
----:----|----:----|----:----|----:----|----:----|----:----|
GCTCGCGTGGGACGCGATGCTCCTGCCGCCGGACCACCTCTAGGCGTCGCTGTAGTTGGA

GATCGAGGACAAGTTCGTGTACCGCGTGGAGTACAAGGGCAGCAACTTCCCCGACGACGG
        1030      1040      1050      1060      1070      1080
----:----|----:----|----:----|----:----|----:----|----:----|
CTAGCTCCTGTTCAAGCACATGGCGCACCTCATGTTCCCGTCGTTGAAGGGGCTGCTGCC

GCCCGTGATGCAGAAGACCATCCTGGGCATCGAGCCCAGCTTCGAGGCCATGTACATGAA
        1090      1100      1110      1120      1130      1140
----:----|----:----|----:----|----:----|----:----|----:----|
CGGGCACTACGTCTTCTGGTAGGACCCGTAGCTCGGGTCGAAGCTCCGGTACATGTACTT

CAACGGCGTGCTGGTGGGCGAGGTGATCCTGGTGTACAAGCTTAACAGCGGCAAGTACTA
        1150      1160      1170      1180      1190      1200
----:----|----:----|----:----|----:----|----:----|----:----|
GTTGCCGCACGACCACCCGCTCCACTAGGACCACATGTTCGAATTGTCGCCGTTCATGAT

CAGCTGCCACATGAAGACCCTGATGAAGAGCAAGGGCGTGGTGAAGGAGTTCCCCAGCTA
        1210      1220      1230      1240      1250      1260
----:----|----:----|----:----|----:----|----:----|----:----|
GTCGACGGTGTACTTCTGGGACTACTTCTCGTTCCCGCACCACTTCCTCAAGGGGTCGAT

CCACTTCATCCAGCACCGCCTCGAGAAGACCTACGTGGAGGACGGCGGCTTCGTGGAGCA
        1270      1280      1290      1300      1310      1320
----:----|----:----|----:----|----:----|----:----|----:----|
GGTGAAGTAGGTCGTGGCGGAGCTCTTCTGGATGCACCTCCTGCCGCCGAAGCACCTCGT

GCACGAGACCGCCATCGCCCAGATGACCAGCATCGGCAAGCCCCTGGGATCCCTGCACGA
        1330      1340      1350      1360      1370      1380
----:----|----:----|----:----|----:----|----:----|----:----|
CGTGCTCTGGCGGTAGCGGGTCTACTGGTCGTAGCCGTTCGGGGACCCTAGGGACGTGCT
```

FIGURE 16D
Restriction map for the GFP Expression vector:

```
            SfiI     NotI         AscI
              \        \            \
GTGGGTGTAGgccgcctcggccGCGGccgcatatggcgcgccGTCGAGCATGCATCTAGG
         1390      1400      1410      1420      1430      1440
----:----|----:----|----:----|----:----|----:----|----:----|
CACCCACATCcggcggagccggCGCCggcgtataccgcgcggCAGCTCGTACGTAGATCC
              /        /            /
            SfiI     NotI         AscI GCGGCCAATTCCGCCCCTCTCCCTCCCCCCCCCCTAACGTTACTGGCCGAAGCCGCTTGG
         1450      1460      1470      1480      1490      1500
----:----|----:----|----:----|----:----|----:----|----:----|
CGCCGGTTAAGGCGGGGAGAGGGAGGGGGGGGGGATTGCAATGACCGGCTTCGGCGAACC AATAAGGCCGGTGTGCGTTTGTCTATATGTGATTTTCCACCATATTGCCGTCTTTTGGCA
         1510      1520      1530      1540      1550      1560
----:----|----:----|----:----|----:----|----:----|----:----|
TTATTCCGGCCACACGCAAACAGATATACACTAAAAGGTGGTATAACGGCAGAAAACCGT ATGTGAGGGCCCGGAAACCTGGCCCTGTCTTCTTGACGAGCATTCCTAGGGGTCTTTCCC
         1570      1580      1590      1600      1610      1620
----:----|----:----|----:----|----:----|----:----|----:----|
TACACTCCCGGGCCTTTGGACCGGGACAGAAGAACTGCTCGTAAGGATCCCCAGAAAGGG CTCTCGCCAAAGGAATGCAAGGTCTGTTGAATGTCGTGAAGGAAGCAGTTCCTCTGGAAG
         1630      1640      1650      1660      1670      1680
----:----|----:----|----:----|----:----|----:----|----:----|
GAGAGCGGTTTCCTTACGTTCCAGACAACTTACAGCACTTCCTTCGTCAAGGAGACCTTC CTTCTTGAAGACAAACAACGTCTGTAGCGACCCTTTGCAGGCAGCGGAACCCCCCACCTG
         1690      1700      1710      1720      1730      1740
----:----|----:----|----:----|----:----|----:----|----:----|
GAAGAACTTCTGTTTGTTGCAGACATCGCTGGGAAACGTCCGTCGCCTTGGGGGGTGGAC GCGACAGGTGCCTCTGCGGCCAAAAGCCACGTGTATAAGATACACCTGCAAAGGCGGCAC
         1750      1760      1770      1780      1790      1800
----:----|----:----|----:----|----:----|----:----|----:----|
CGCTGTCCACGGAGACGCCGGTTTTCGGTGCACATATTCTATGTGGACGTTTCCGCCGTG
```

FIGURE 16E
Restriction map for the GFP Expression vector:

```
AACCCCAGTGCCACGTTGTGAGTTGGATAGTTGTGGAAAGAGTCAAATGGCTCTCCTCAA
          1810      1820      1830      1840      1850      1860
----:----|----:----|----:----|----:----|----:----|----:----|
TTGGGGTCACGGTGCAACACTCAACCTATCAACACCTTTCTCAGTTTACCGAGAGGAGTT

GCGTATTCAACAAGGGGCTGAAGGATGCCCAGAAGGTACCCCATTGTATGGGATCTGATC
          1870      1880      1890      1900      1910      1920
----:----|----:----|----:----|----:----|----:----|----:----|
CGCATAAGTTGTTCCCCGACTTCCTACGGGTCTTCCATGGGGTAACATACCCTAGACTAG

TGGGGCCTCGGTGCACATGCTTTACATGTGTTTAGTCGAGGTTAAAAAAACGTCTAGGCC
          1930      1940      1950      1960      1970      1980
----:----|----:----|----:----|----:----|----:----|----:----|
ACCCCGGAGCCACGTGTACGAAATGTACACAAATCAGCTCCAATTTTTTGCAGATCCGG

CCCCGAACCACGGGGACGTGGTTTTCCTTTGAAAAACACGATGataatatggccacaacc
          1990      2000      2010      2020      2030      2040
----:----|----:----|----:----|----:----|----:----|----:----|
GGGGCTTGGTGCCCCTGCACCAAAAGGAAACTTTTTGTGCTACtattataccggtgttgg TTCTAAATACATTCAAATATGTATCCGCTCATGAGACAATAAtatTGATAtaggaggtat
          2050      2060      2070      2080      2090      2100
----:----|----:----|----:----|----:----|----:----|----:----|
AAGATTTATGTAAGTTTATACATAGGCGAGTACTCTGTTATTataACTATatcctccata aaatATGggatcggccATTGAACAAGATGGATTGCACGCAGGTTCTCCGGCCGCTTGGGT
          2110      2120      2130      2140      2150      2160
----:----|----:----|----:----|----:----|----:----|----:----|
tttaTACcctagccggTAACTTGTTCTACCTAACGTGCGTCCAAGAGGCCGGCGAACCCA GGAGAGGCTATTCGGCTATGACTGGGCACAACAGACAATCGGCTGCTCTGATGCCGCCGT
          2170      2180      2190      2200      2210      2220
----:----|----:----|----:----|----:----|----:----|----:----|
CCTCTCCGATAAGCCGATACTGACCCGTGTTGTCTGTTAGCCGACGAGACTACGGCGGCA GTTCCGGCTGTCAGCGCAGGGGCGCCCGGTTCTTTTTGTCAAGACCGACCTGTCCGGTGC
          2230      2240      2250      2260      2270      2280
----:----|----:----|----:----|----:----|----:----|----:----|
CAAGGCCGACAGTCGCGTCCCCGCGGGCCAAGAAAAACAGTTCTGGCTGGACAGGCCACG
```

FIGURE 16F
Restriction map for the GFP Expression vector:

```
CCTGAATGAACTGCAAGACGAGGCAGCGCGGCTATCGTGGCTGGCCACGACGGGCGTTCC
          2290      2300      2310      2320      2330      2340
----:----|----:----|----:----|----:----|----:----|----:----|
GGACTTACTTGACGTTCTGCTCCGTCGCGCCGATAGCACCGACCGGTGCTGCCCGCAAGG

TTGCGCAGCTGTGCTCGACGTTGTCACTGAAGCGGGAAGGGACTGGCTGCTATTGGGCGA
          2350      2360      2370      2380      2390      2400
----:----|----:----|----:----|----:----|----:----|----:----|
AACGCGTCGACACGAGCTGCAACAGTGACTTCGCCCTTCCCTGACCGACGATAACCCGCT

AGTGCCGGGGCAGGATCTCCTGTCATCTCACCTTGCTCCTGCCGAGAAAGTATCCATCAT
          2410      2420      2430      2440      2450      2460
----:----|----:----|----:----|----:----|----:----|----:----|
TCACGGCCCCGTCCTAGAGGACAGTAGAGTGGAACGAGGACGGCTCTTTCATAGGTAGTA

GGCTGATGCAATGCGGCGGCTGCATACGCTTGATCCGGCTACCTGCCCATTCGACCACCA
          2470      2480      2490      2500      2510      2520
----:----|----:----|----:----|----:----|----:----|----:----|
CCGACTACGTTACGCCGCCGACGTATGCGAACTAGGCCGATGGACGGGTAAGCTGGTGGT

AGCGAAACATCGCATCGAGCGAGCACGTACTCGGATGGAAGCCGGTCTTGTCGATCAGGA
          2530      2540      2550      2560      2570      2580
----:----|----:----|----:----|----:----|----:----|----:----|
TCGCTTTGTAGCGTAGCTCGCTCGTGCATGAGCCTACCTTCGGCCAGAACAGCTAGTCCT

TGATCTGGACGAAGAACATCAGGGGCTCGCGCCAGCCGAACTGTTCGCCAGGCTCAAGGC
          2590      2600      2610      2620      2630      2640
----:----|----:----|----:----|----:----|----:----|----:----|
ACTAGACCTGCTTCTTGTAGTCCCCGAGCGCGGTCGGCTTGACAAGCGGTCCGAGTTCCG

GAGCATGCCCGACGGCGAGGATCTCGTCGTGACCCATGGCGATGCCTGCTTGCCGAATAT
          2650      2660      2670      2680      2690      2700
----:----|----:----|----:----|----:----|----:----|----:----|
CTCGTACGGGCTGCCGCTCCTAGAGCAGCACTGGGTACCGCTACGGACGAACGGCTTATA

CATGGTGGAAAATGGCCGCTTTTCTGGATTCATCGACTGTGGCCGGCTGGGTGTGGCGGA
          2710      2720      2730      2740      2750      2760
----:----|----:----|----:----|----:----|----:----|----:----|
GTACCACCTTTTACCGGCGAAAAGACCTAAGTAGCTGACACCGGCCGACCCACACCGCCT
```

FIGURE 16G
Restriction map for the GFP Expression vector:

```
CCGCTATCAGGACATAGCGTTGGCTACCCGTGATATTGCTGAAGAACTTGGCGGCGAATG
         2770      2780      2790      2800      2810      2820
----:----|----:----|----:----|----:----|----:----|----:----|
GGCGATAGTCCTGTATCGCAACCGATGGGCACTATAACGACTTCTTGAACCGCCGCTTAC

GGCTGACCGCTTCCTCGTGCTTTACGGTATCGCCGCTCCCGATTCGCAGCGCATCGCCTT
         2830      2840      2850      2860      2870      2880
----:----|----:----|----:----|----:----|----:----|----:----|
CCGACTGGCGAAGGAGCACGAAATGCCATAGCGGCGAGGGCTAAGCGTCGCGTAGCGGAA

BstB1
                         \
CTATCGCCTTCTTGACGAGTTCTTCTGAttcgaaGACCGACCAAGCGACGCCCAACCTGC
         2890      2900      2910      2920      2930      2940
----:----|----:----|----:----|----:----|----:----|----:----|
GATAGCGGAAGAACTGCTCAAGAAGACTaagcttCTGGCTGGTTCGCTGCGGGTTGGACG
                                /
                              AsuII CATCACGAGATTTCGATTCCACCGCCGCCTTCTATGAAAGGTTGGGCTTCGGAATCGTTT
         2950      2960      2970      2980      2990      3000
----:----|----:----|----:----|----:----|----:----|----:----|
GTAGTGCTCTAAAGCTAAGGTGGCGGCGGAAGATACTTTCCAACCCGAAGCCTTAGCAAA TCCGGGACGCCGGCTGGATGATCCTCCAGCGCGGGGATCTCATGCTGGAGTTCTTCGCCC
         3010      3020      3030      3040      3050      3060
----:----|----:----|----:----|----:----|----:----|----:----|
AGGCCCTGCGGCCGACCTACTAGGAGGTCGCGCCCCTAGAGTACGACCTCAAGAAGCGGG ACCCTAGGGGGAGGCTAACTGAAACACGGAAGGAGACAATACCGGAAGGAACCCGCGCTA
         3070      3080      3090      3100      3110      3120
----:----|----:----|----:----|----:----|----:----|----:----|
TGGGATCCCCCTCCGATTGACTTTGTGCCTTCCTCTGTTATGGCCTTCCTTGGGCGCGAT TGACGGCAATAAAAAGACAGAATAAAACGCACGGTGTTGGGTCGTTTGTTCATAAACGCG
         3130      3140      3150      3160      3170      3180
----:----|----:----|----:----|----:----|----:----|----:----|
ACTGCCGTTATTTTTCTGTCTTATTTTGCGTGCCACAACCCAGCAAACAAGTATTTGCGC GGGTTCGGTCCCAGGGCTGGCACTCTGTCGATACCCCACCGAGACCCCATTGGGGCCAAT
         3190      3200      3210      3220      3230      3240
----:----|----:----|----:----|----:----|----:----|----:----|
CCCAAGCCAGGGTCCCGACCGTGAGACAGCTATGGGGTGGCTCTGGGGTAACCCCGGTTA
```

FIGURE 16H
Restriction map for the GFP Expression vector:

```
ACGCCCGCGTTTCTTCCTTTTCCCCACCCCACCCCCCAAGTTCGGGTGAAGGCCCAGGGC
          3250      3260      3270      3280      3290      3300
----:----|----:----|----:----|----:----|----:----|----:----|
TGCGGGCGCAAAGAAGGAAAAGGGGTGGGGTGGGGGGTTCAAGCCCACTTCCGGGTCCCG

TCGCAGCCAACGTCGGGGCGGCAGGCCCTGCCATAGCCTCAGGTTACTCATATATACTTT
          3310      3320      3330      3340      3350      3360
----:----|----:----|----:----|----:----|----:----|----:----|
AGCGTCGGTTGCAGCCCCGCCGTCCGGGACGGTATCGGAGTCCAATGAGTATATATGAAA

AGATTGATTTAAAACTTCATTTTTAATTTAAAAGGATCTAGGTGAAGATCCTTTTTGATA
          3370      3380      3390      3400      3410      3420
----:----|----:----|----:----|----:----|----:----|----:----|
TCTAACTAAATTTTGAAGTAAAAATTAAATTTTCCTAGATCCACTTCTAGGAAAAACTAT

ATCTCATGACCAAAATCCCTTAACGTGAGTTTTCGTTCCACTGAGCGTCAGACCCCGTAG
          3430      3440      3450      3460      3470      3480
----:----|----:----|----:----|----:----|----:----|----:----|
TAGAGTACTGGTTTTAGGGAATTGCACTCAAAAGCAAGGTGACTCGCAGTCTGGGGCATC

AAAAGATCAAAGGATCTTCTTGAGATCCTTTTTTTCTGCGCGTAATCTGCTGCTTGCAAA
          3490      3500      3510      3520      3530      3540
----:----|----:----|----:----|----:----|----:----|----:----|
TTTTCTAGTTTCCTAGAAGAACTCTAGGAAAAAAAGACGCGCATTAGACGACGAACGTTT

CAAAAAAACCACCGCTACCAGCGGTGGTTTGTTTGCCGGATCAAGAGCTACCAACTCTTT
          3550      3560      3570      3580      3590      3600
----:----|----:----|----:----|----:----|----:----|----:----|
GTTTTTTTGGTGGCGATGGTCGCCACCAAACAAACGGCCTAGTTCTCGATGGTTGAGAAA

TTCCGAAGGTAACTGGCTTCAGCAGAGCGCAGATACCAAATACTGTCCTTCTAGTGTAGC
          3610      3620      3630      3640      3650      3660
----:----|----:----|----:----|----:----|----:----|----:----|
AAGGCTTCCATTGACCGAAGTCGTCTCGCGTCTATGGTTTATGACAGGAAGATCACATCG

CGTAGTTAGGCCACCACTTCAAGAACTCTGTAGCACCGCCTACATACCTCGCTCTGCTAA
          3670      3680      3690      3700      3710      3720
----:----|----:----|----:----|----:----|----:----|----:----|
GCATCAATCCGGTGGTGAAGTTCTTGAGACATCGTGGCGGATGTATGGAGCGAGACGATT
```

FIGURE 16I
Restriction map for the GFP Expression vector:

```
TCCTGTTACCAGTGGCTGCTGCCAGTGGCGATAAGTCGTGTCTTACCGGGTTGGACTCAA
         3730      3740      3750      3760      3770      3780
----:----|----:----|----:----|----:----|----:----|----:----|
AGGACAATGGTCACCGACGACGGTCACCGCTATTCAGCACAGAATGGCCCAACCTGAGTT

GACGATAGTTACCGGATAAGGCGCAGCGGTCGGGCTGAACGGGGGGTTCGTGCACACAGC
         3790      3800      3810      3820      3830      3840
----:----|----:----|----:----|----:----|----:----|----:----|
CTGCTATCAATGGCCTATTCCGCGTCGCCAGCCCGACTTGCCCCCAAGCACGTGTGTCG

CCAGCTTGGAGCGAACGACCTACACCGAACTGAGATACCTACAGCGTGAGCTATGAGAAA
         3850      3860      3870      3880      3890      3900
----:----|----:----|----:----|----:----|----:----|----:----|
GGTCGAACCTCGCTTGCTGGATGTGGCTTGACTCTATGGATGTCGCACTCGATACTCTTT

GCGCCACGCTTCCCGAAGGGAGAAAGGCGGACAGGTATCCGGTAAGCGGCAGGGTCGGAA
         3910      3920      3930      3940      3950      3960
----:----|----:----|----:----|----:----|----:----|----:----|
CGCGGTGCGAAGGGCTTCCCTCTTTCCGCCTGTCCATAGGCCATTCGCCGTCCCAGCCTT

CAGGAGAGCGCACGAGGGAGCTTCCAGGGGGAAACGCCTGGTATCTTTATAGTCCTGTCG
         3970      3980      3990      4000      4010      4020
----:----|----:----|----:----|----:----|----:----|----:----|
GTCCTCTCGCGTGCTCCCTCGAAGGTCCCCCTTTGCGGACCATAGAAATATCAGGACAGC

GGTTTCGCCACCTCTGACTTGAGCGTCGATTTTTGTGATGCTCGTCAGGGGGGCGGAGCC
         4030      4040      4050      4060      4070      4080
----:----|----:----|----:----|----:----|----:----|----:----|
CCAAAGCGGTGGAGACTGAACTCGCAGCTAAAAACACTACGAGCAGTCCCCCCGCCTCGG

TATGGAAAAACGCCAGCAACGCGGCCTTTTTACGGTTCCTGGCCTTTTGCTGGCCTTTTG
         4090      4100      4110      4120      4130      4140
----:----|----:----|----:----|----:----|----:----|----:----|
ATACCTTTTTGCGGTCGTTGCGCCGGAAAAATGCCAAGGACCGGAAAACGACCGGAAAAC

CTCACATGTTCTTTCCTGCGTTATCCCCTGATTCTGTGGATAACCGTATTACCGCC
         4150      4160      4170      4180      4190      4200
----:----|----:----|----:----|----:----|----:----|----:----|
GAGTGTACAAGAAAGGACGCAATAGGGGACTAAGACACCTATTGGCATAATGGCGG
```

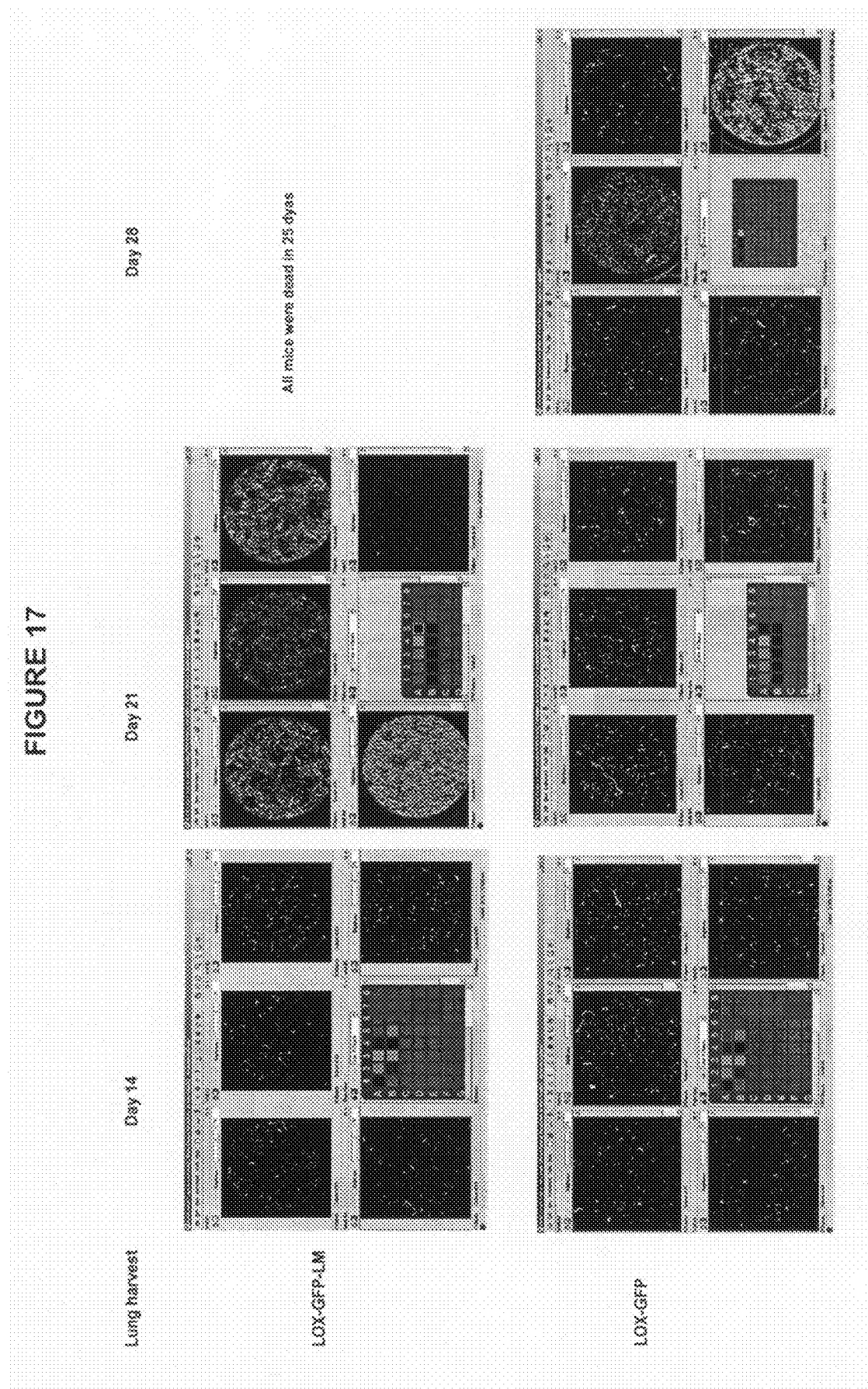

FIGURE 19

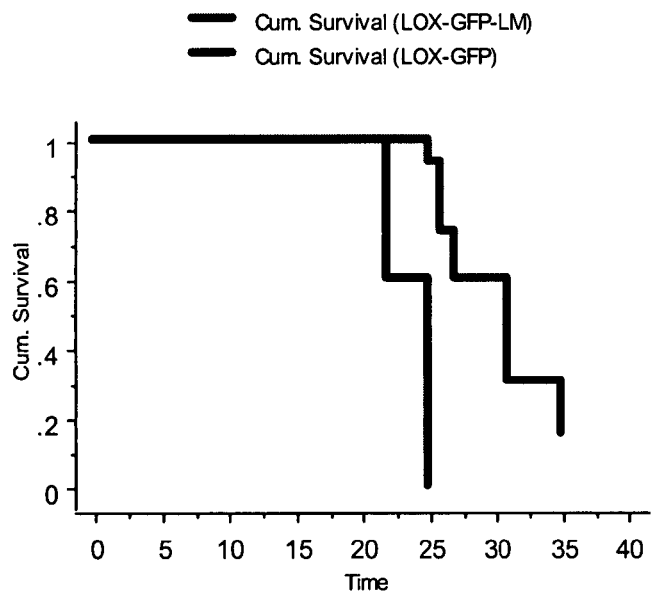

Logrank (Mantel-Cox) Test for days
Censor Variable: censor
Grouping Variable: Cells

| Chi-Square | DF | P-Value |
|---|---|---|
| 25.511 | 1 | <.0001 |

Kaplan-Meier Survival Statistics for days
Censor Variable: censor
Grouping Variable: Cells

|  | Estimate | Std. Error |
|---|---|---|
| LOX-GFP-LM 25% | 22.000 | 3.162 |
| LOX-GFP-LM 50% | 25.000 | · |
| LOX-GFP-LM 75% | 25.000 | · |
| LOX-GFP-LM Mean | 23.800 | .393 |
| LOX-GFP 25% | 26.000 | .685 |
| LOX-GFP 50% | 31.000 | 2.894 |
| LOX-GFP 75% | 35.000 | 3.565 |
| LOX-GFP Mean | 30.267 | 1.122 |

One or more estimates of the mean are biased because the last observation in those strata/groups were censored.

TUMOR MODELS EMPLOYING GREEN FLUORESCENT PROTEIN

PRIORITY TO RELATED APPLICATIONS

This application claims the benefit of U.S. Provisional Application No. 60/788,250, filed Mar. 31, 2006, which is hereby incorporated by reference in its entirety.

BACKGROUND OF THE INVENTION

Several examples of utilizing peritoneal (ascites) tumor growth to assess the activity of chemotherapeutics have been reported in the literature, including one that utilized LOX melanoma cells. For example, R. H. Shoemaker et al., *Proc. Am. Assoc. Cancer Res.*, 26:330 (1985), reported that LOX melanoma cells could form ascites, and that the model could be used to assess cancer therapeutics by using a survival endpoint around day 20. In 2003, H. Nakanishi et al., *Cancer Sci.*, 94:112-118 (2003), reported a peritoneal model utilizing gastric cancer cells tagged with GFP. This model was used to study the chemosensitivity of peritoneal cell growth to an anti-cancer agent. Tumor burden was measured by harvesting GFP cells from the peritoneal cavity, homogenizing the cells, centrifuging cells at 10000 g, and then measuring the fluorescence of the supernatant using a fluorescence counter. In order to extrapolate the number of cells that produced the fluorescence, a calibration curve was used with a standard number of GFP cells. In this model, >1 month was needed for ascites production in the peritoneum.

Several examples of utilizing metastatic tumor growth to assess the activity of chemotherapeutics have been reported in the literature. The LOX experimental metastasis model was reported by O. Fodstad et al., *Int. J. Cancer*, 41:442-449 (1988), by R. H. Shoemaker et al. in 1991, and by M. Yeng et al., *Clin. Cancer Res.*, 5:3549-3559, (1999) with GFP-tagged cells.

For example, Fodstad et al. reported that LOX cells injected into the tail vein of immunocompromised mice were able to metastasize to lung with nearly 100% frequency. The size and number of colonies differed from one animal to another however, and thus the authors found it was not possible to establish an accurate relationship between the cell number injected and resulting colony number. For this reason, they used animal survival as an endpoint rather than counting metastatic colonies on the lungs.

In a report by R. H. Shoemaker et al. 1991, LOX-L cells were generated by 16 cycles of subcutaneous (sc) tumor transplantation, followed by removal of a lung metastasis for growth in vitro. Unlike the parental cell line LOX, the LOX-L cell line was able to metastasize to lung from sc tumor implantation, whereas LOX cells could only metastasize from iv implantation. LOX-L sc tumors were utilized to study the effects of chemotherapeutics on metastasis, however the authors went through the very arduous procedure of transplanting metastatic lungs into new mice for evaluation of pulmonary metastases. In subsequent studies (Wang X et al., *Int. J. Cancer*, 112:994-1002, 2004) the LOX-L model was implanted iv, however metastases were evaluated simply by counting colonies and utilizing a survival endpoint.

In a report by M. Yeng et al., *Clin. Cancer Res.*, 5:3549-4559 (1999), metastasis models were established utilizing GFP tagged LOX or B16 melanoma cells. For the LOX-GFP model, tumors were implanted orthotopically (transdermally), whereas for B16 GFP model, cells were implanted iv. GFP was used to identify lung metastases, however the authors failed to quantify the lung metastatic tumor burden, and instead used a subjective (qualitative) endpoint. They simply visualized metastases in live animals or upon necropsy by utilizing a fluorescent microscope to establish the presence or absence of metastases.

SUMMARY OF THE INVENTION

The human melanoma cell line LOX can induce either ascites when tumor cells are implanted intra-peritoneally, or lung metastasis when inoculated intravenously. The ascites model can be used as a fast drug-screening model, whereas the lung metastasis model may be useful to evaluate antimetastatic agents. In both models, quantitative analysis of tumor growth and efficacy has been a challenge due to difficulties in assessing tumor burden. To resolve this issue, the present invention provides LOX cells transfected with GFP (called LOX-GFP), and this marker was utilized to analyze tumor burden in ascites or in lung.

For the ascites model, $10 \times 10^6$ LOX-GFP cells were inoculated intra-peritoneally in Nu/Nu mice, and ascites were harvested after 7 days. Ascites was visualized under a fluorescence microscope and relative fluorescence was quantitated utilizing Acumen Explorer. Anti-proliferative efficacy in this model was validated using a cytotoxic agent, Taxol, as well as some development compounds.

For the lung metastasis model, a new cell line called LOX-GFP-LM was established; this cell line was isolated from a lung metastasis colony in mice which was induced through intravenous inoculation of LOX-GFP cells. The LOX-GFP-LM cell line reproducibly colonizes lung 25-30 days post IV inoculation of $2 \times 10^6$ cells. Lungs were harvested and visualized under a fluorescence microscope, and the relative fluorescence of homogenized lung suspension was assessed utilizing Acumen Explorer. Anti-metastatic efficacy was validated in this model utilizing two development compounds previously shown to have broad and potent anti-tumor activity in traditional subcutaneous xenograft studies. To compare two new cell lines (LOX-GFP and LOX-GFP-LM) with the parental cell line (LOX), gene array analysis and tumor histopathology were characterized.

The present invention provides application of GFP to two human melanoma LOX models in mice, resulting in better quantitative tumor burden assessment and improved efficacy evaluation. These improved models should provide a feasible alternative for ascites or experimental metastasis evaluation of novel cancer therapeutics.

The present invention provides a method of evaluating whether a tumor metastasizes which comprises injecting GFP-expressing tumor cells intravenously into an athymic mouse, such as a nude or SCID mouse, followed by sacrificing the mouse and removing one or more tissues to be evaluated. The removed tissue is homogenized, and the level of GFP in the homogenized sample quantified using laser-scanning fluoroscopy, e.g. an Acumen Explorer.

The present invention also provides a method for evaluating a candidate drug or protocol for the inhibition of metastasis of a tumor which comprises injecting an athymic mouse intravenously with GFP-expressing tumor cells and administering a candidate drug or protocol to the mouse. The mouse is then sacrificed and one or more tissues removed for evaluation of metastasis inhibition. The removed tissue is homogenized and the level of GFP in a homogenized sample of the tissue quantified using laser-scanning fluoroscopy. The GFP level is compared to the level of GFP in a homogenized sample from a control animal which has not been treated with the candidate drug or protocol. A decreased level of GFP in the treated sample as compared to the control sample denotes inhibition of metastasis.

The present invention further provides a method for evaluating a candidate drug or protocol for the treatment of a tumor which comprises injecting an athymic mouse intraperitoneally with GFP-expressing tumor cells and administering a candidate drug or protocol to the mouse. Ascites or an organ containing the tumor is removed for evaluation and the level of GFP in a sample of the ascites of homogenized tissue is quantified using laser-scanning fluoroscopy. The level of GFP in the ascites or homogenized sample is then compared to that from a control animal which has not been treated with the candidate drug or protocol. A decreased level of GFP in the treated sample as compared to the control sample denotes that the candidate drug or protocol is useful in the treatment of said tumor.

The present invention provides a method of enhancing the propensity of a tumor cell line to metastasize to a particular tissue which comprises injecting an athymic mouse intraperitoneally with tumor cells that express GFP, removing the ascites formed in the mouse and injecting it intravenously into another athymic mouse. The mouse is sacrificed, and the tissue to which metastasis is to be enhanced is removed. GFP-expressing tumor cells are then recovered from the removed tissue, cultured in vitro, and injected into an athymic mouse, where the cultured tumor cells metastasize to the tissue from which the cells were recovered to a greater degree than the original GFP-expressing tumor cells.

The present invention further provides a LOX-GFP-LM cell line which metastasizes to lung to a greater degree than the parental LOX-GFP cell line. This cell line provides advantages in the assays described herein.

DESCRIPTION OF THE FIGURES

FIGS. 2A through 2M show Affymetrix microarray data isolated from LOX, LOX-GFP, and LOX-GFP-LM cells demonstrating the effect of these cells on the indicated genes.

FIG. 3 indicates the relative fluorescence units (RFU) of ascites samples for [4-Amino-2-(1-methanesulfonyl-piperidin-4-ylamino)-pyrimidin-5-yl]-(2,3-difluoro-6-methoxy-phenyl)-methanone (Compound A) run on an Acumen Explorer.

FIG. 4 depicts the relative fluorescence units (RFU) of ascites samples for 4-[4,5-Bis-(4-chloro-phenyl)-2-(2-isopropoxy-4-methoxy-phenyl)-4,5-dihydro-imidazole-1-carbonyl]-piperazin-2-one (Compound B) and 5-(4-Ethoxy-quinolin-6-ylmeth-(Z)-ylidine)-2-(2-hydroxy-1-(R)-phenyl-ethylamino)-thiazol-4-one (Compound C) run on an Acumen Explorer.

FIG. 5 depicts the relative fluorescence units (RFU) of ascites samples for 4-[(4S,5R)-4,5-Bis-(4-chloro-phenyl)-2-(2-isopropoxy-4-methoxy-phenyl)-4,5-dihydro-imidazole-1-carbonyl]-piperazin-2-one (Compound D) and for the combination of Taxol and Compound D run on an Acumen Explorer.

FIG. 16 (a-i) depicts the restriction map for the GFP expression vector.

FIG. 17 provides photographs of lung homogenate sample wells of mice injected either with LOX-GFP or with LOX-GFP-LM tumor lines. Lungs were harvested at 14, 21, and 28 days post-injection.

FIG. 19 provides Kaplan-Meier survival curves both LOX-GFP and LOX-GFP-LM tumor lines in SCID beige mice.

DETAILED DESCRIPTION OF THE INVENTION

Figure 1:
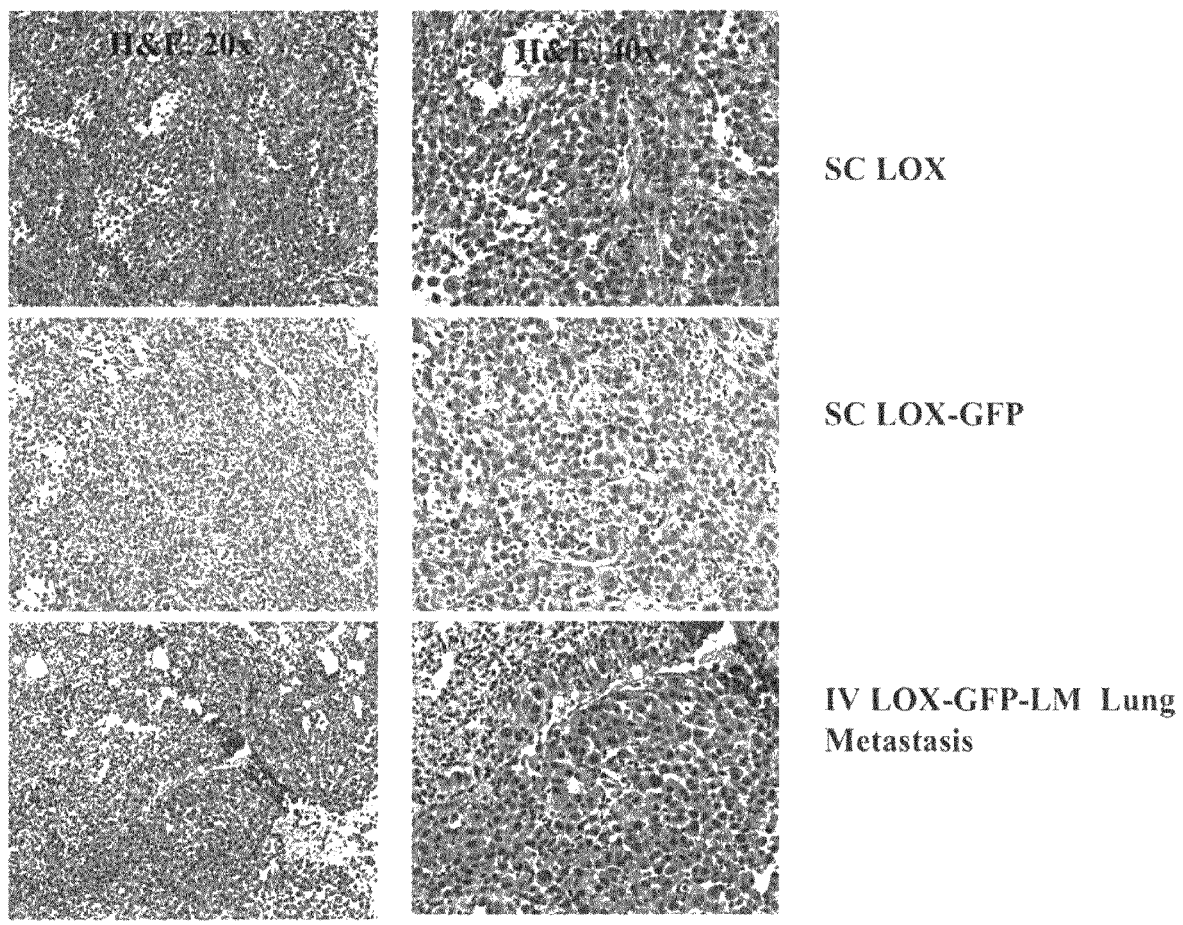
FIG. 1 illustrates the morphology of LOX, LOX-GFP, and LOX-GFP-LM tumors in SCID beige mice.

The present invention provides several key modifications over the LOX peritoneal (ascites) models previously used to produce a model having a much shorter duration than those previously employed. The present model allows for rapid quantification of cell number as an endpoint. Although the duration for previous studies was fairly short at only 20 days, the current model does not rely on survival as the sole endpoint, and can be completed in as little as 7 days.

The current model utilizes cells tagged with GFP, however the method of ascites quantification has been improved by eliminating the homogenization and centrifugation steps. The process of the invention directly measures cell number from ascites using the Acumen Explorer.

The present invention provides significant improvements to the LOX experimental metastasis models described previously by stably transfecting GFP into the cells, so that lungs can be removed and metastatic tumor burden can be accurately quantified by measuring fluorescence. This method reduces reliance on survival as an endpoint (although it may sometimes be monitored when scientifically relevant). The model of the present invention utilizes an experimental metastatic model using iv implantation of LOX cells rather than using LOX-L cells. Additionally, metastases is quantified using GFP-tagged cells rather than relying on colony counts and survival, as those methods are not accurate enough to discern small differences in metastatic tumor burden.

In the model of the invention, the metastatic tumor burden is quantified in order to accurately assess the anti-metastatic capability of experimental therapeutics using various treatment schedules. Therefore the step of visualizing metastases in vivo was omitted in favor of removing the lungs, homogenizing them, and measuring the relative fluorescence of lungs from vehicle treated Vs. therapeutic treated mice.

In one aspect, the present invention provides a stable clone of the LOX melanoma cell line expressing green fluorescent protein (GFP) and an assay for evaluating the anti-tumor efficacy of potential clinical candidate therapeutics, i.e. drugs and protocols, in vivo. In particular, the invention provides two different in vivo models; 1) a short (7-10 day) peritoneal (ascites) model for rapid screening of compounds for efficacy, and 2) an experimental metastasis model for assessment of the anti-metastatic capabilities of novel cancer therapeutics.

In another aspect, the present invention provides a peritoneal (ascites) model for rapid screening of the anti-tumor efficacy of potential cancer clinical candidate therapeutics in vivo. The model is unique in that it provides efficacy data in as little as 7 days and provides quantitative rather than qualitative data.

In still another aspect, the present invention provides an experimental metastasis model for evaluating the anti-metastatic efficacy of potential cancer clinical candidate therapeutics in vivo. The model is unique in that it provides quantified data regarding metastatic tumor burden rather than relying on survival as the sole endpoint.

Bicistronic construct denotes a mammalian expression vector containing two genes inserted into expression vector. Bicistronic GFP construct denotes a mammalian expression vector, preferably pCMV-tag 5A (Stratagene, Genbank accession number AF076312), which has been modified to contain a nucleotide sequence encoding a GFP molecule, preferably GFP from *Renilla mullerei*, and a nucleotide sequence encoding Neo (Neomycin resistant gene) for G418 selection.

A spontaneous metastasis model is one in which a primary tumor is established in an animal and is allowed to grow and spread to secondary sites without any manipulation or intervention. This process requires that the cells from the primary tumor gain entry into the circulatory system through their natural capability, and then seed and grow in distant sites.

An experimental metastasis model is one in which a primary tumor is not established. Cells are directly injected into the circulatory system to mimic the seeding and growth process of metastasis to distant sites.

Green Fluorescent Protein (GFP) is a luminescent protein produced by species of soft coral. GFP can be obtained from a variety of different sources, including *Renilla mullerei*, *Renilla reniformis*, *Renilla kollikeri Aeruorea victoria*. While any GFP molecule can be used in the present invention, the preferred GFP is from *Renilla mullerei*.

LOX-GFP cell line is a cell line created by transfection of LOX melanoma cells obtained from National Cancer Institute (NCI) with the bicistronic GFP construct described above.

LOX-GFP-LM cell line is a cell line created by injecting athymic mice intraperitoneally with LOX-GFP cells, removing ascites containing LOX-GFP cells from the mice, injecting said ascites intravenously into mice, collecting the resultant metastatic lungs from the mice, and culturing colonies of GFP-expressing tumor cells recovered from the metastatic lung tissue in vitro.

Tumor cells that stably express green fluorescent protein can be prepared in the following manner. Tumor cells from an established tumor cell line can be transfected in a conventional manner with a bicistronic GFP construct prepared in accordance with the procedure in Example 1. For example, Fugene, a multi-component lipid-based (non-liposomal) transfection reagent (Roche Molecular Diagnostics) can be added to a serum free medium, such as RPMI1640, followed by addition of the bicistronic GFP construct. While the ratio of Fugene to construct can vary, the ratio is advantageously 3:1. The sample is incubated, for example at room temperature, for a period of about 30 minutes, and the mixture transferred to a flask of tumor cells. The tumor cells are present in culture at a ration of about 80%. The cells are incubated for a period of about 6 hours, followed by removal of the incubation medium and addition of a selection medium containing 1% Geneticin (G418).

Selection for G418 resistance will take a few weeks, for example 3 to 6 weeks, after which the cells are sorted for those which show the greatest GFP expressions. The top 5% GFP expressing cell population are then selected, isolated, grown up, and further sorted to obtain cells having 100% GFP expression.

Tumor cells that metastasize to a particular tissue more aggressively than the corresponding parental tumor cell line can be prepared in the following manner. Athymic mice are implanted, preferably intra-peritoneally (ip), with approximately 10 to 20 million GFP-expressing tumor cells each. After about 10 to 14 days, ascites fluid containing the GFP-expressing tumor cells is harvested from the mice, and the ascites diluted with PBS. The ascites/PBS solution is filtered through a 40 μm nylon cell strainer and centrifuged at about 1500 rpm. Pelleted cells are resuspended in PBS and counted to achieve the desired cell concentration.

Athymic mice are then transplanted intravenously (iv), for example via the tail vein, with the GFP-expressing tumor cells isolated from ascites (above). The cells are preferably transplanted at a concentration between about $1 \times 10^6$ cell/mouse and about $2 \times 10^6$ cell/mouse. Once the mice are moribund or dead, the tissue of interest, for example lung or breast tissue, is isolated and examined under a fluorescence stereomicroscope to see potential micro-metastases.

Colonies of GFP-expressing tumor cells which show very strong expression are recovered from the tissue, for example by gentle dissection. The colonies can then be ground on sterile metal gauze (#40), washed with 2-3 ml culture medium, and centrifuged at about 1500 rpm. The cell pellets can then be washed in a serum free medium, such as RPMI1640 culture medium which preferably contains about 10% penicillin/streptomycin and about 10% fetal bovine serum (FBS). The cells are seeded into flasks of RPMI1640 medium containing about 10% FBS and about 2% penicillin/streptomycin. The cells are routinely passaged in selection medium containing G418 to remove any mouse cell contaminants. After several, preferably 2-3, passages, cultures can be scaled up and frozen down for future use. The cells will metastasize to the tissue from which they were isolated to a greater extent than the original GFP-expressing tumor cells. This ability can be shown by the following assay. Hereinafter, these will be referred to as enhanced metastatic tumor cells (EMTC).

Athymic mice are implanted iv with approximately $1 \times 10^6$ to about $5 \times 10^6$ EMTC into the tail vein. At approximately 25 to 30 days post implantation, moribundity or mortality is assessed, and the mice are euthanized. The tissue to which the cells are expected to metastasize is isolated and homogenized in PBS. A sample, e.g. 0.1 ml, of the homogenized tissue is transferred to a 96 well plate and fluorescence is measured via laser-scanning fluoroscopy, for example using an Acumen Explorer.

The cell lines prepared and evaluated by the above procedures are valuable for the evaluation of candidate therapies, in particular clinical drug candidates and protocols, for the treatment of cancer and/or inhibition of metastasis. For evaluation of candidate therapies against tumors, GFP-expressing tumor cells in PBS are injected intra-peritoneally (ip) into athymic mice. Preferably about 10 million cells in a volume of about 500 μl PBS are injected. The mice are divided into control and treatment groups, and the treatment groups are treated with the candidate drug or protocol. It should be understood that the GFP-expressing tumor cells can be injected into the mice first, followed by treatment with the candidate drug or protocol, or the candidate drug or protocol can be administered followed by injection of the mice with GFP-expressing tumor cells.

The ascites is harvested by euthanizing the mice and aspirating the ascites fluid from the peritoneum. The peritoneal cavity is rinsed with saline, which is then recovered. The ascites and the recovered saline are transferred to a tube, filtered through a 40 μm nylon filter to obtain a single cell suspension, and centrifuged at about 1500 rpm for a period of about 10 minutes. The supernatant is removed, and the cell pellet resuspended in fresh saline. A sample, e.g. 0.1 ml, from each mouse is transferred into a 96 well plate to evaluate cell number (reported as relative fluorescence units) utilizing laser-scanning fluoroscopy, for example, an Acumen Explorer. If the treated mice show a lower relative fluorescence than the control group, the candidate therapy is useful for the treatment of that type tumor.

For evaluation of candidate therapies for inhibiting metastasis, enhanced metastatic tumor cells maintained in RPMI 1640 medium plus 10% FBS and 1% Geneticin (G418) are injected intravenously into athymic mice via the tail vein. Preferably about 2 million cells in a volume of about 200 μl serum free RPMI1640 are employed. The mice are randomized into control and treatment groups, and the treatment groups are treated with the candidate drug or protocol. It should be understood that the EMTCs can be injected into the mice first, followed by treatment with the candidate drug or protocol, or the candidate drug or protocol can be administered followed by injection of the mice with EMTCs. When the control mice are moribund or when they die, their metastatic tumor burden evaluated.

In addition to survival, a quantitative evaluation of anti-metastatic efficacy can be made using the present invention by measuring the fluorescence intensity of tissue homogenates. Live mice are euthanized, and tissue to be evaluated is removed and homogenized in saline. A sample of the tissue homogenate, e.g. 0.2 ml, from each mouse is transferred to a 96 well plate, and fluorescence is then read using laser-scanning fluoroscopy, e.g. an Acumen Explorer. Using this method, the amount of metastasis as compared to the control group can be determined. If the treated my show a lower metastatic tumor burden, the candidate drug inhibits metastasis.

EXAMPLES

Example 1

Preparation of Bicistronic GFP Construct

Figure 15:
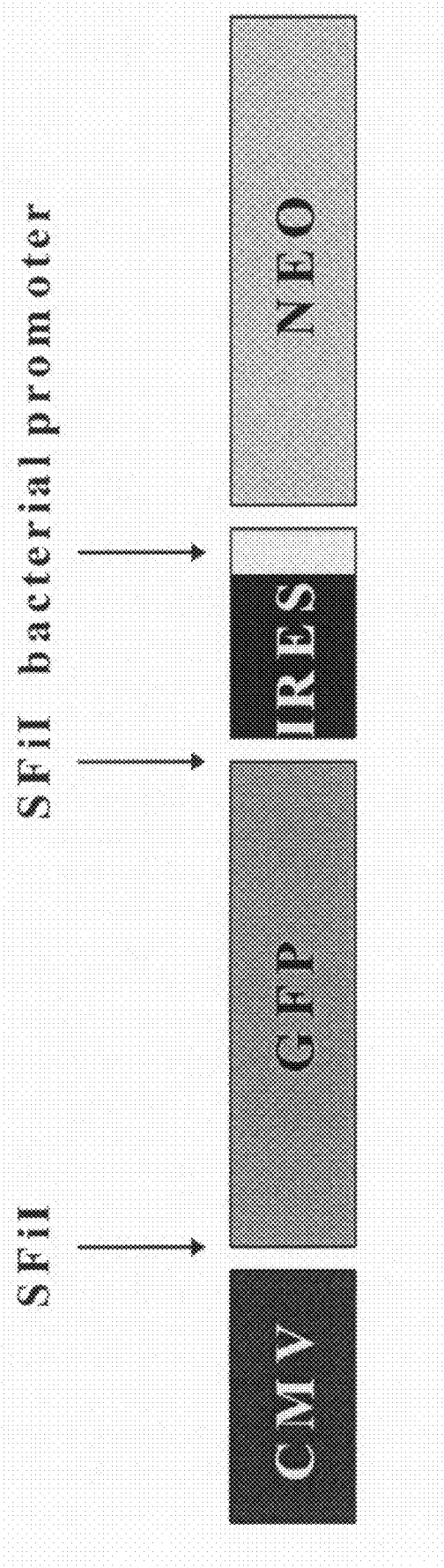
FIG. 15 is a simple schematic of the crucial portions of a pCMV-tag 5A plasmid containing GFP and Neo.

The bicistronic GFP construct was prepared and provided by Anne Chua and Ueli Gubler, and contained genes for both *Renilla mulleri* GFP (Prolume Ltd., Pinetop, Ariz.) and the Neomycin phosphotransferase (Neomycin resistant marker) for G418 selection. The sequence of the *R. mulleri* GFP was engineered into a mammalian expression vector as follows. The vector "pCMV-tag 5A" (Stratagene, Genbank accession number AF076312) was first modified by removing the sequence fragment between the single NotI and BstBI sites. This leaves a plasmid backbone consisting of the ColE1 origin of replication, the HSV-TK polyA sequence and the CMV promoter. The deleted fragment was then replaced with a fragment encoding an [IRES-Neomycin phosphotransferase resistance marker]. The IRES-sequence was disabled based on the principle described by e.g. Rees et al, Biotechniques 20:102, 1996, incorporated by reference herein. The disabling fragment was chosen to represent the bacterial beta-lactamase ("bla") promoter; this strategy allowed for the use of the neomycin-phosphotransferase marker for plasmid selection in *E. coli* (Kanamycin). In a third step, the ORF for the *R. mulleri* GFP was inserted upstream of the IRES sequence, in between two SfiI sites. The HSV-TK sequence that is located downstream of the NEO-resistance gene serves as a polyA signal sequence for expression in mammalian cells. A simple schematic of the crucial portions of this plasmid is shown in FIG. 15.

Example 2

Preparation of Bicistronic GFP Construct

The sequence of *R. mulleri* GFP was engineered for stable expression in mammalian cells using a specifically designed modular vector. The construct was prepared and provided by Ann Chua and Ueli Gubler, and contained genes for both *Renilla mulleri* GFP (Prolume Ltd., Pinetop, Ariz.) and the Neomycin phosphotransferase (Neomycin resistant marker) for G418 selection. The sequence of the *R. mulleri* GFP was engineered into a mammalian expression vector as follows.

Step 1

The vector "pCMV-tag 5A" (Stratagene, Genbank accession number AF076312) was first modified by removing the sequence fragment between the single NotI and BstBI sites. This leaves a plasmid backbone consisting of the ColEl origin of replication, the HSV-TK polyA sequence and the CMV promoter.

Step 2

By overlap-PCR, a module of having the general makeup 5'-AscI-IRES-Neomycin phosphotransferase-BstB1-3' was generated. Within this module, the IRES-sequence was disabled based on the principle described by e.g. Rees et al, Biotechniques 20:102, 1996, incorporated by reference herein. The disabling fragment was chosen to represent the bacterial beta-lactamase ("bla") promoter (Seq ID No. 1); this strategy allowed for the use of the neomycin-phosphotransferase marker for plasmid selection in *E. coli* (Kanamycin) as well as selection of mammalian cells in G418. It also eliminated the need for an extra transcription unit for plasmid selection in *E. coli*, making the final plasmid smaller.

Step 3

The plasmid-derived NotI/BstbI module from step 1 and the AscI-IRES-Neo-BstbI module from step 2 were subsequently ligated and circularized by addition of a synthetic short AscI to NotI-linker. DNA was transformed and single isolates were checked for proper assembly of the three fragments. A properly assembled plasmid clone was selected for the last modification.

Step 4

The cloning sites for the gene of interest (GFP) were subsequently introduced into the plasmid via a short synthetic linker of the structure EcoRV-SfiIa-stuffer-SfiIb-NotI. This linker was cloned into the plasmid derived in step 3 via ligation in between the OliI-NotI sites, thus placing it upstream of the IRES-NEO module. OliI and EcoRV are both blunt-end cutters, making them compatible for ligation without recreating the sites. The rationale behind using SfiI sites for cloning the gene of interest was twofold: SfiI is an 8-base cutter and thus occurs very infrequently as internal sites in ORFs chosen for expression in this vector. The site has the recognition sequence ggccnnnnnggcc (Seq ID No. 2), allowing the design of two different sites at either end of an ORF for directional cloning. The sequence 5'-ggccattatggcc-3' (Seq ID No. 3) was chosen as the SfiI-a (upstream) site, while the SfiI-b (downstream) site has the sequence 5'-ggccgcctcggcc-3' (Seq ID No. 4).

Step 5

The ORF for the *R. mulleri* GFP engineered to have the appropriate SfiI sites was inserted upstream of the IRES sequence, in between two SfiI sites, resulting in a plasmid of 4196 bp length (Seq ID No. 5). The restriction map for the GFP Expression Vector is provided in FIG. 16.

Example 3

Establishment of LOX-GFP Cells

Cell Transfection

Cells from the human melanoma cell line LOX (National Cancer Institute) were cultured in RPMI1640 medium RPMI1640 medium with 10% fetal bovine serum (FBS). All culture medium and related reagents were purchased from Gibco (Invitrogen Corporation, Carlsbad, Calif.). Cells were transfected using Fugene (Roche Molecular Diagnostics) transfecting reagent at a ratio of 3:1 (Fugene:DNA). The bicistronic GFP construct was kindly prepared and provided by Ann Chua and Ueli Gubler in accordance with Example 1. The construct contained genes for both *Renilla mullerei* (Prolume Ltd., Pinetop, Ariz.) and Neo (Neomycin resistant gene) for G418 selection.

100 μl of RPMI1640 serum free medium was added to a small sterile tube, and then 9 μl pre-warmed Fugene was added. Finally, 3 μl GFP DNA construct was added to the bottom of the tube, mixed, and incubated at room temperature for 30 min. The entire Fugene/DNA mixture was added to one T-25 flask of 80% confluent LOX cells, and the cells were incubated for 6 hrs. Following incubation, the medium in the flask was removed and replaced with selection medium containing 1% Geneticin (G418).

Selection for G418 resistance took about four weeks, after which approximately 30% of cells expressed GFP at various levels. To further select for the most highly GFP expressing cells, the cells were sorted at the Department of Pathology and Pediatrics, UMDNJ. Cells were sorted to collect the top 5% GFP expressing cell population. Cells isolated and grown up from the first sort were subsequently sorted a few weeks later, so that the resulting cells achieved 100% GFP expression. These LOX-GFP cells were then frozen down for future in vivo use.

Example 4

Establishment of LOX-GFP-LM Cells

Five female Nu/Nu mice (Charles River) were implanted intra-peritoneally (ip) with 10 million LOX-GFP cells each. After 13 days, ascites fluid containing LOX-GFP cells was harvested from the mice, and the ascites was diluted 1:4 with PBS. The ascites/PBS solution was then filtered through a 40 μm nylon cell strainer and centrifuged at 1500 rpm. Pelleted cells were resuspended in PBS and counted to achieve the desired cell concentration.

Twenty female Nu/Nu mice (10 mice/group) were implanted intravenously (iv) via the tail vein with the LOX-GFP tumor cells isolated from ascites (above) at either $2\times10^6$ cell/mouse or $1\times10^6$ cell/mouse. After a few mice in the group were found moribund or dead, the remaining mice in the group were euthanized. Lungs were isolated and examined under a fluorescence stereomicroscope to see potential micrometastases. The resultant iv LOX-GFP lung metastases are listed in Table 1.

TABLE 1

LOX-GFP ascites implantation into Nu/Nu mice.

| Days post-implantation | $2 \times 10^6$ cell/mouse | $1 \times 10^6$ cell/mouse |
|---|---|---|
| Day 36 | 5 mice dead<br>2 mice with lung metastases with moderate GFP expression.<br>3 mice had no signs of metastasis | |
| Day 59 | | 2 mice dead<br>2 mice with lung metastases with no GFP expression.<br>1 mouse (No. 10) had lung metastases with strong GFP expression 5 mice had no signs of metastasis |

It appeared that the rate of metastasis to lung was not as high as reported in the literature, which might cause difficulty for quantitative analysis. Some metastatic colonies lost GFP expression, suggesting the cell line was not stable in vivo. One mouse (No. 10) from the $1 \times 10^6$ cell group had very strong GFP expression in the lung metastatic colonies.

Four colonies of LOX-GFP cells (about 2×3 mm) were recovered from the lung of mouse No. 10 (see above), by gentle dissection. Each of the colonies was ground separately on sterile metal gauze (#40), washed with 2-3 ml culture medium and centrifuged at 1500 rpm. Cell pellets were washed in RPMI1640 culture medium containing 10% penicillin/streptomycin and 10% FBS and were seeded into T-25 flasks containing 10 ml of RPMI1640 medium containing 10% FBS and 2% penicillin/streptomycin. The cells were routinely passaged in selection medium containing G418 to remove any mouse cell contaminants. After 2-3 passages, cultures from colony numbers 1 and 2 were discarded due to weak GFP expression and poor growth. Cultures from colony numbers 3 and 4 were scaled up and frozen down for future use. Cells from colony number 4 were deemed superior in terms of GFP expression and growth and were named LOX-GFP-LM (LM for Lung Metastasis).

Example 5

Metastasis of LOX-GFP-LM Cells In Vivo

Thirty female SCID beige mice (Charles River) were implanted iv with one, two, or five million LOX-GFP-LM cells into the tail vein. At day 29 post implantation, moribundity or mortality from each group up to that point was recorded, and the remaining mice were euthanized. Lungs were isolated and homogenized in 3 ml of PBS per sample. 0.1 ml per sample of lung homogenate was transferred into a 96 well plate and fluorescence was measured using an Acumen Explorer. After 29 days post-implantation, the incidence of morbidity or mortality was directly related to the cell number implanted, with the highest morbidity and mortality rate observed in mice implanted with 5 million cells (Table 2.) All mice had GFP expressing lung metastatic colonies, however the number and density of the lung metastases varied greatly.

TABLE 2

LOX-GFP-LM induced experimental lung metastases in SCID beige mice.

| Group | Morbidity/ Mortality Day 29 | Lung Metastases Present | GFP Expression Observed in Lung Metastases | Relative Fluorescence Units of Lung Homogenates (mean ± SD) |
|---|---|---|---|---|
| $5 \times 10^6$ cells/ mouse | 7/10 | 3/3 | 3/3 | Not assessed |
| $2 \times 10^6$ cells/ mouse | 4/10 | 6/6 | 6/6 | 58457423 ± 52009858 |
| $1 \times 10^6$ cells/ mouse | 2/10 | 8/8 | 8/8 | 45712175 ± 30253653 |

Example 6

Characterization of LOX-GFP-LM, LOX-GFP, and LOX Cells

Morphology of LOX, LOX-GFP, and LOX-GFP-LM Tumors In Vivo:

Nine female SCID beige mice (Charles River) were implanted subcutaneously (sc) with either LOX or LOX-GFP cells, or were implanted iv with LOX-GFP-LM cells. LOX and LOX-GFP tumors were allowed to grow until they reached a volume of ~300-400 mm$^3$ (about 10-14 days post implantation) and were then collected and fixed in 10% formalin. LOX-GFP-LM cells were allowed to develop lung metastases over 29 days, and then portions of the lung were harvested and fixed in 10% Formalin. Both tumor and lung samples were stained with H & E and morphology was assessed. No difference in morphology between the tumors derived from the three different LOX tumor cell lines (LOX, LOX-GFP and LOX-GFP-LM) was observed (FIG. 1).

Example 7

Gene Microarray Analysis of LOX, LOX-GFP, and LOX-GFP-LM Cell Lines

Cells were plated in 6 well culture plates with RPMI-1640, 10% FBS, and 1% Penicillin/Streptomycin (plus 0.5% G418 for LOX-GFP and LOX-GFP-LM cells), and incubated for 48 hours. After removing medium, the cells were washed once with PBS, 0.8 ml of RLT buffer was added per well, and the plate was shaken for 2 min at room temperature. Cell suspensions from each well were transferred into separate tubes and were frozen at −80° C. for future microarray analysis. Four separate samples from each tumor line were run in the microarray assay using Affymetrix U133plus2 chips. Unique gene signatures were shown for both LOX-GFP and LOX-GFP-LM cells as compared to the LOX parental cell line. (FIG. 2) In LOX-GFP-LM cells, 124 genes were found to be altered overall, with 67 genes up-regulated and the remaining 57 genes down-regulated, as compared to LOX-GFP cells. Among the genes with at least 4 fold up-regulation, a series of genes (at least 7 genes, marked in bold) were recognized to be related adhesion, matrix degradation, or angiogenesis. Another category of genes (marked in underline) were recognized as related to growth factors or differentiation. Both series of genes comprise the type of genes that might be expected to be enriched in a cell population with a more aggressive and invasive phenotype.

Example 8

LOX-GFP Peritoneal (Ascites) Model

Human melanoma LOX-GFP cells, prepared in accordance with the procedure of Example 3, were maintained in RPMI 1640 medium plus 10% FBS, and 1% Geneticin (G418). Female Nu/Nu mice were injected intra-peritoneally (ip) with 10 million LOX-GFP cells in a volume of 500 μl PBS, randomized into groups, and treated as shown in Tables 3, 4, and 5 with a variety of doses and/or dose schedules.

Compounds Tested

[4-Amino-2-(1-methanesulfonyl-piperidin-4-ylamino)-pyrimidin-5-yl]-(2,3-difluoro-6-methoxy-phenyl)-methanone (Compound A)

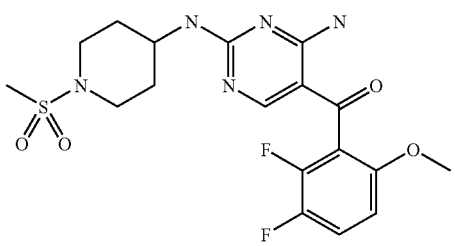

4-[4,5-Bis-(4-chloro-phenyl)-2-(2-isopropoxy-4-methoxy-phenyl)-4,5-dihydro-imidazole-1-carbonyl]-piperazin-2-one (Compound B)

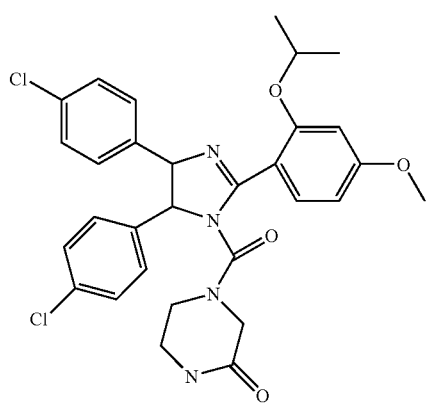

5-(4-Ethoxy-quinolin-6-ylmeth-(Z)-ylidine)-2-(2-hydroxy-1-(R)-phenyl-ethylamino)-thiazol-4-one (Compound C)

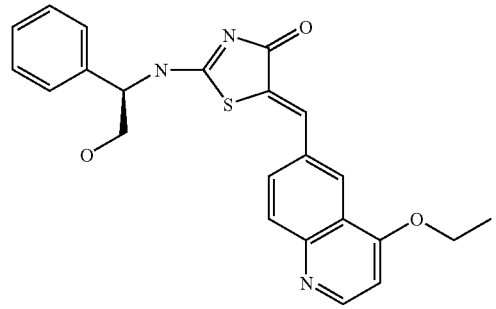

4-[(4S,5R)-4,5-Bis-(4-chloro-phenyl)-2-(2-isopropoxy-4-methoxy-phenyl)-4,5-dihydro-imidazole-1-carbonyl]-piperazin-2-one (Compound D)

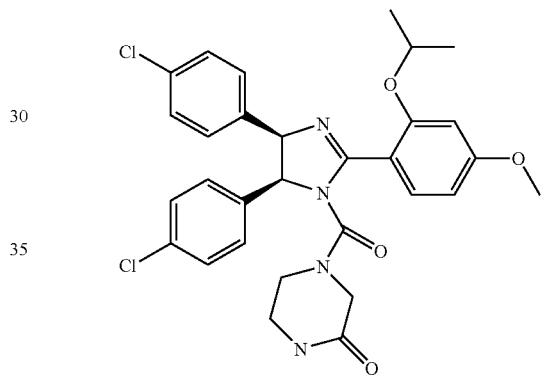

TABLE 3

Treatment groups for LOX-GFP Ascites model.

| Group | iv cell injection Day 0 | Treatment | Number of mice | Days dosed (after cell injection) | Day of ascites harvest |
|---|---|---|---|---|---|
| 1 | 10 × 10⁶ cells/mouse | Vehicle for Taxol | 2 | Days 4, 5, & 6 | Day 7 |
| 2 | | Taxol 10 mg/kg iv, 0.2 ml, 3 doses | 2 | Days 4, 5, & 6 | Day 7 |
| 3 | | Taxol 10 mg/kg iv, 0.2 ml, 2 doses | 2 | Days 5 & 6 | Day 7 |
| 4 | | Taxol 10 mg/kg iv, 0.2 ml, single dose | 2 | Day 6 | Day 7 |
| 5 | | Vehicle for Compound A | 2 | Days 4, 5, & 6 | Day 7 |
| 6 | | Compound A 40 mg/kg po, 0.2 ml, 3 doses | 2 | Days 4, 5, & 6 | Day 7 |
| 7 | | Compound A 40 mg/kg po, 0.2 ml, 2 doses | 2 | Days 5 & 6 | Day 7 |
| 8 | | Compound A 40 mg/kg po, 0.2 ml, single dose | 2 | 6 Day 6 | Day 7 |

TABLE 4

Treatment groups for LOX-GFP Ascites model.

| Group | Tumor cell implanted (day 0) | Treatment | Number of mice | Days dosed (after cell injection) | Day of ascites harvest |
|---|---|---|---|---|---|
| 1 | $10 \times 10^6$ cells/mouse | Vehicle for Compound B | 5 | Days 2, 3, 4.5, 6 & 7 | Day 8 |
| 2 |  | Compound B 40 mg/kg sc, 0.2 ml, 6 doses | 5 | Days 2, 3, 4.5, 6 & 7 | Day 8 |
| 3 |  | Vehicle for Compound B | 5 | Days 2, 3, 4.5, 6 & 7 | Day 8 |
| 4 |  | Compound C 200 mg/kg po bid, 0.2 ml, 12 doses | 5 | Days 2, 3, 4.5, 6 & 7 | Day 8 |
| 5 |  | Vehicle for Taxol | 5 | Days 5, 6 & 7 | Day 8 |
| 6 |  | Taxol 15 mg/kg iv, 0.2 ml, 3 doses | 5 | Days 5, 6 & 7 | Day 8 |

TABLE 5

Treatment groups for LOX-GFP Ascites model.

| Group | Tumor cell implanted (day 0) | Treatment | Number of mice | Days dosed (after cell injection) | Day of ascites harvest |
|---|---|---|---|---|---|
| 1 | $10 \times 10^6$ cells/mouse | Vehicle for Compound D Compound D 100 mg/kg po bid, 0.2 ml, 6 doses | 4 4 | Days 4, 5 & 6 Days 4, 5 & 6 | Day 7 Day 7 |
| 2 |  | Compound D 50 mg/kg po bid, 0.2 ml, 6 doses | 4 | Days 4, 5 & 6 | Day 7 |
| 3 |  | Compound D 25 mg/kg po bid, 0.2 ml, 6 doses | 4 | Days 4, 5 & 6 | Day 7 |
| 4 |  | Taxol 15 mg/kg iv, 0.2 ml, 2 doses | 4 | Days 5 & 6 | Day 7 |
| 5 |  | Taxol 15 mg/kg iv, 0.2 ml, 2 doses + Compound D 100 mg/kg po bid, 0.2 ml, 6 doses | 4 | Days 5 & 6 (Taxol) Days 4, 5 & 6 (Compound D) | Day 7 |
| 6 |  | Taxol 15 mg/kg iv, 0.2 ml, 2 doses + Compound D 50 mg/kg po bid, 0.2 ml, 6 doses | 4 | Days 5 & 6 (Taxol) Days 4, 5 & 6 (Compound D) | Day 7 |
| 7 |  | Taxol 15 mg/kg iv, 0.2 ml, 2 doses + Compound D 25 mg/kg po bid, 0.2 ml, 6 doses | 4 | Days 5 & 6 (Taxol) Days 4, 5 & 6 (Compound D) | Day 7 |

Ascites Harvesting Procedure (at Day 7 or 8 Post Implantation):

Mice were euthanized, and then a small incision was made along the midline of the abdomen through the skin and peritoneum. A glass Pasteur pipet was utilized to aspirate and remove ascites fluid from the peritoneum, and the ascites was transferred to a 15 ml tube. 3 ml saline was used to rinse the peritoneal cavity, and all of the saline was recovered and transferred into the 15 ml tube containing the ascites fluid. The ascites cell suspension was filtered through a 40 μm nylon filter to obtain a single cell suspension and centrifuged at 1500 rpm for 10 min. The supernatant was removed, and the cell pellet was resuspended in 2 ml of fresh saline. 0.1 ml from each sample was transferred into a 96 well plate to evaluate cell number (reported as relative fluorescence units) utilizing an Acumen Explorer.

Results

Figure 6:
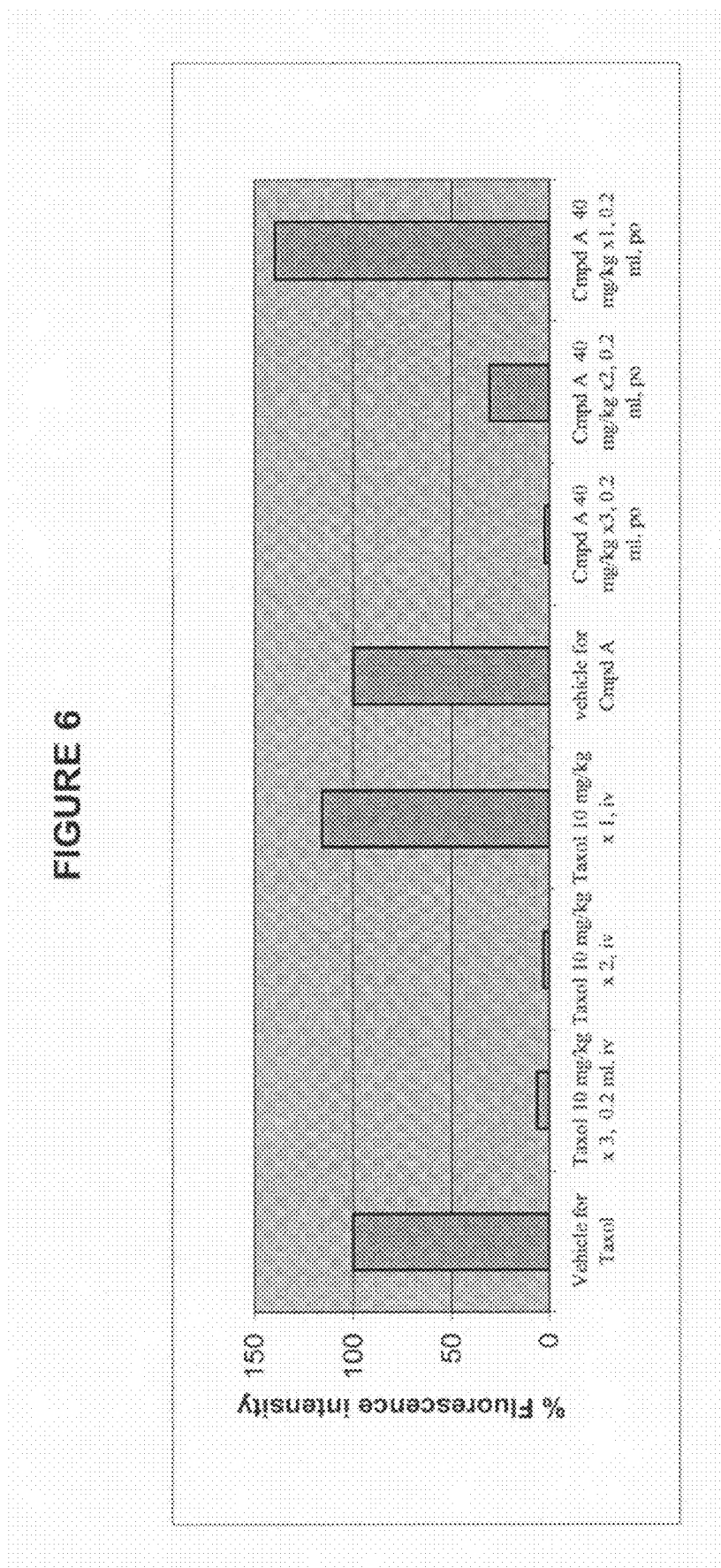
FIG. 6 illustrates the percent fluorescent intensity of ascites samples from Nu/Nu mice treated with [4-Amino-2-(1-methanesulfonyl-piperidin-4-ylamino)-pyrimidin-5-yl]-(2,3-difluoro-6-methoxy-phenyl)-methanone (Compound A) as compared to Vehicle control group.
Figure 7:
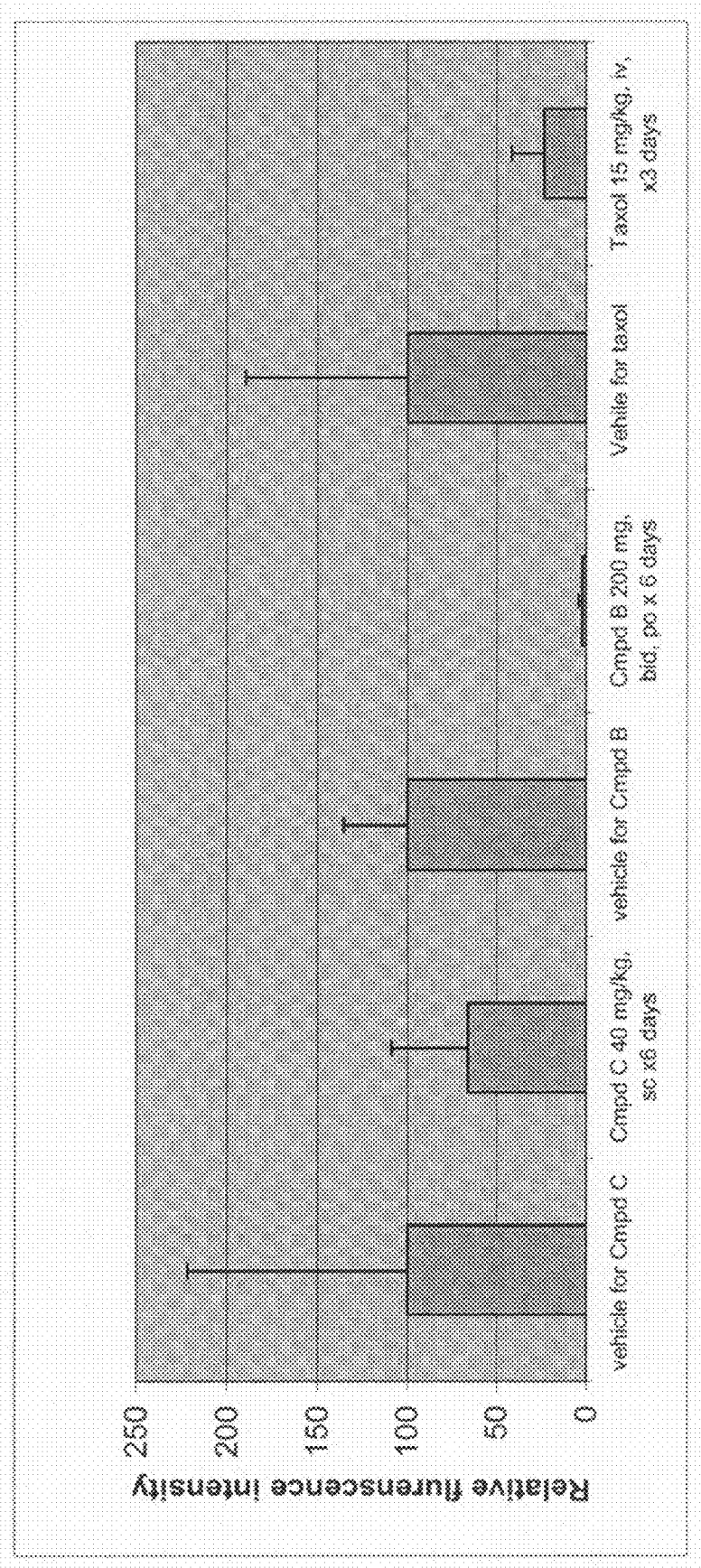
FIG. 7 illustrates the percent fluorescent intensity of ascites samples from Nu/Nu mice treated with 4-[4,5-Bis-(4-chloro-phenyl)-2-(2-isopropoxy-4-methoxy-phenyl)-4,5-dihydro-imidazole-1-carbonyl]-piperazin-2-one (Compound B) or 5-(4-Ethoxy-quinolin-6-ylmeth-(Z)-ylidine)-2-(2-hydroxy-1-(R)-phenyl-ethylamino)-thiazol-4-one (Compound C) as compared to Vehicle control group.
Figure 8:
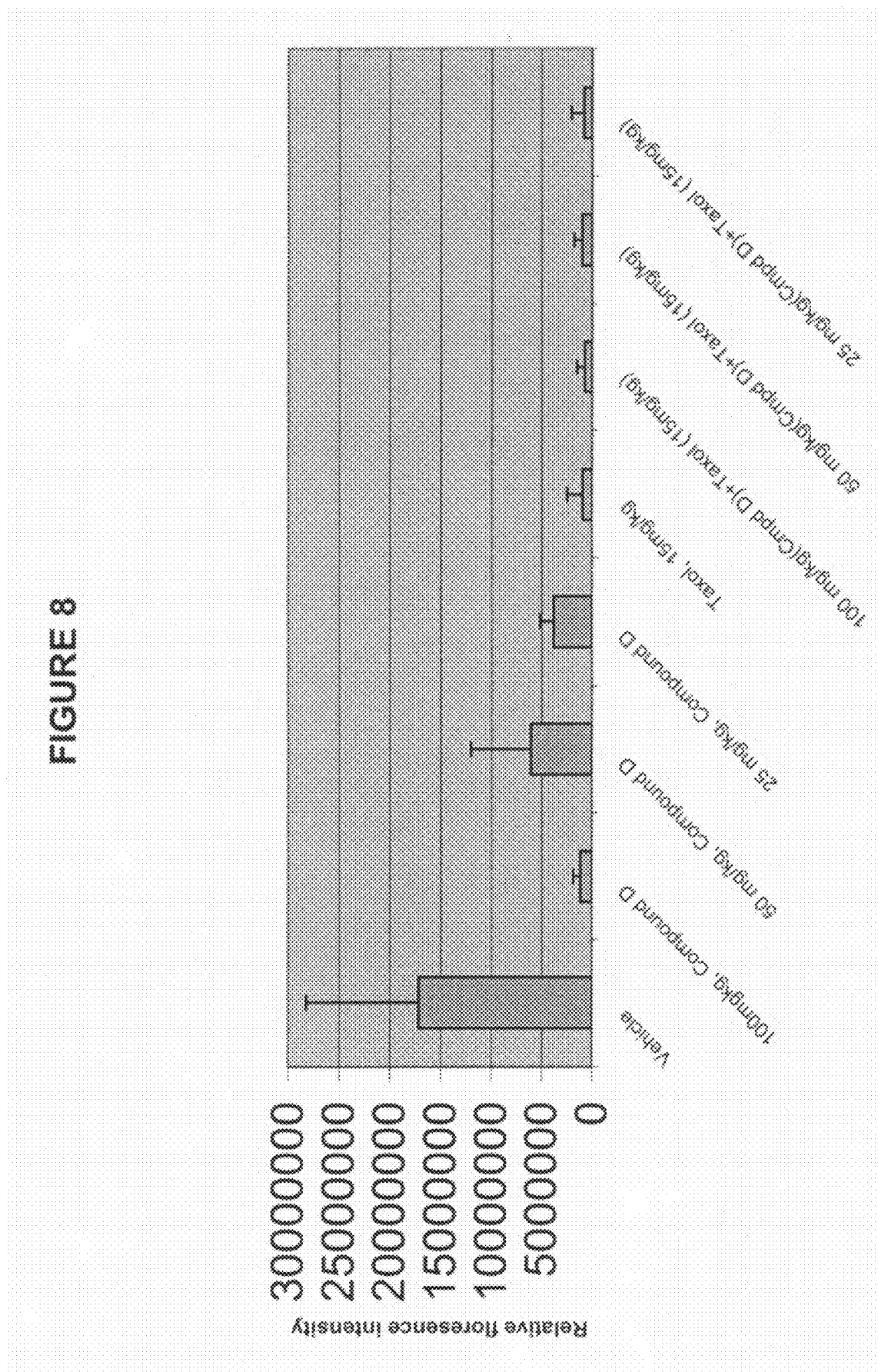
FIG. 8 illustrates the percent fluorescent intensity of ascites samples from Nu/Nu mice treated with 4-[(4S,5R)-4,5-Bis-(4-chloro-phenyl)-2-(2-isopropoxy-4-methoxy-phenyl)-4,5-dihydro-imidazole-1-carbonyl]-piperazin-2-one (Compound D) or with the combination of Taxol and Compound D as compared to Vehicle control group.

Seven or eight days was a sufficient duration for adequate ascites to form in mice implanted ip with LOX-GFP cells, and additionally was sufficient to measure the growth inhibitory properties of cancer therapeutics administered systemically. Both Taxol and Compound A demonstrated inhibitory effects on LOX-GFP ascites growth that was directly dependent on the number of treatments. A single dose did not inhibit cell growth, whereas two doses reduced cell growth, and three doses reduced cell growth maximally. (FIGS. 3 and 6). Both Compound B and Compound C demonstrated inhibitory effects on LOX-GFP ascites growth. (FIGS. 4 and 7). Compound D inhibited LOX-GFP ascites growth at several doses, however the effect was not dose-dependent. With regard to ascites growth inhibition, there was no added benefit to combining Compound D with Taxol as compared to Taxol alone, however the combination was not antagonistic. (FIGS. 5 and 8).

Example 9

LOX-GFP-LM Metastasis Model

Human melanoma LOX-GFP-LM cells, prepared in accordance with the procedure of Example 4, were maintained in RPMI 1640 medium plus 10% FBS and 1% Geneticin (G418). Female SCID beige mice were injected iv via the tail vein with 2 million cells in a volume of 200 μl serum free RPMI1640, randomized into groups, and treated as shown in Tables 6 and 7 with a variety of doses and/or dose schedules. When >3 mice in the Vehicle treated group were found moribund, five mice per treatment group were removed to evaluate metastatic lung tumor burden. The remaining mice from each group were monitored for survival benefit until they were moribund.

Compounds Tested

4-[(4S,5R)-4,5-Bis-(4-chloro-phenyl)-2-(2-isopropoxy-4-methoxy-phenyl)-4,5-dihydro-imidazole-1-carbonyl]-piperazin-2-one (Compound D)

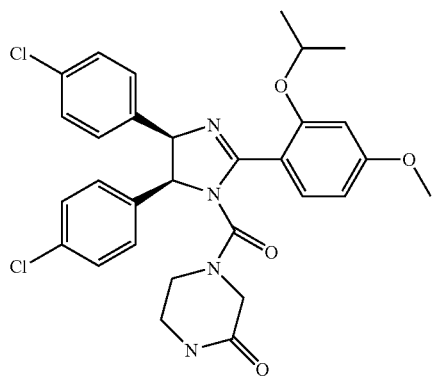

3-methyl-5-(2-chlorophenyl)-7-amino-pyrazolo[3,4][1,4]benzodiazepine (Compound E)

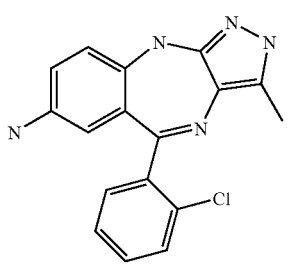

TABLE 6

Treatment groups for LOX-GFP-LM experimental metastasis model (Compound E Study)

| Groups | Tumor cells injected (day 0) | Treatment | Number of mice | Days of dosing after cell injection | Day of lung harvest (5 mice/group) |
|---|---|---|---|---|---|
| 1 | 2 × 10⁶ cells/mouse | Vehicle | 20 | Day −1 to 21 | 25 |
| 2 | | Compound E 5 mg/kg po, bid | 15 | Day −1 to 21 (7+/4−schedule) | 25 |
| 3 | | | 15 | Day −1 to 7 | 25 |
| 4 | | | 15 | Day 3 to 21 (4+/3−schedule) | 25 |

TABLE 7

Treatment groups for LOX-GFP-LM experimental metastasis model (Compound D Study)

| Groups | Tumor cell implanted (day 0) | medication | Number of mice | Days of dosing after cell injection | Day of lung harvest (5 mice/group) |
|---|---|---|---|---|---|
| 1 | 2 × 10⁶ cells/mouse | Vehicle | 20 | Day −1 to 21 | 26 |
| 2 | | Compound D 200 mg/kg po, bid | 15 | Day −1 to 21 | 26 |
| 3 | | | 15 | Day −1 to 7 | 26 |
| 4 | | | 15 | Day 3 to 21 | 26 |

Two parameters were assessed for quantitative evaluation of anti-metastatic efficacy: 1) Fluorescence intensity of lung homogenates and 2) Survival.

Figure 9:
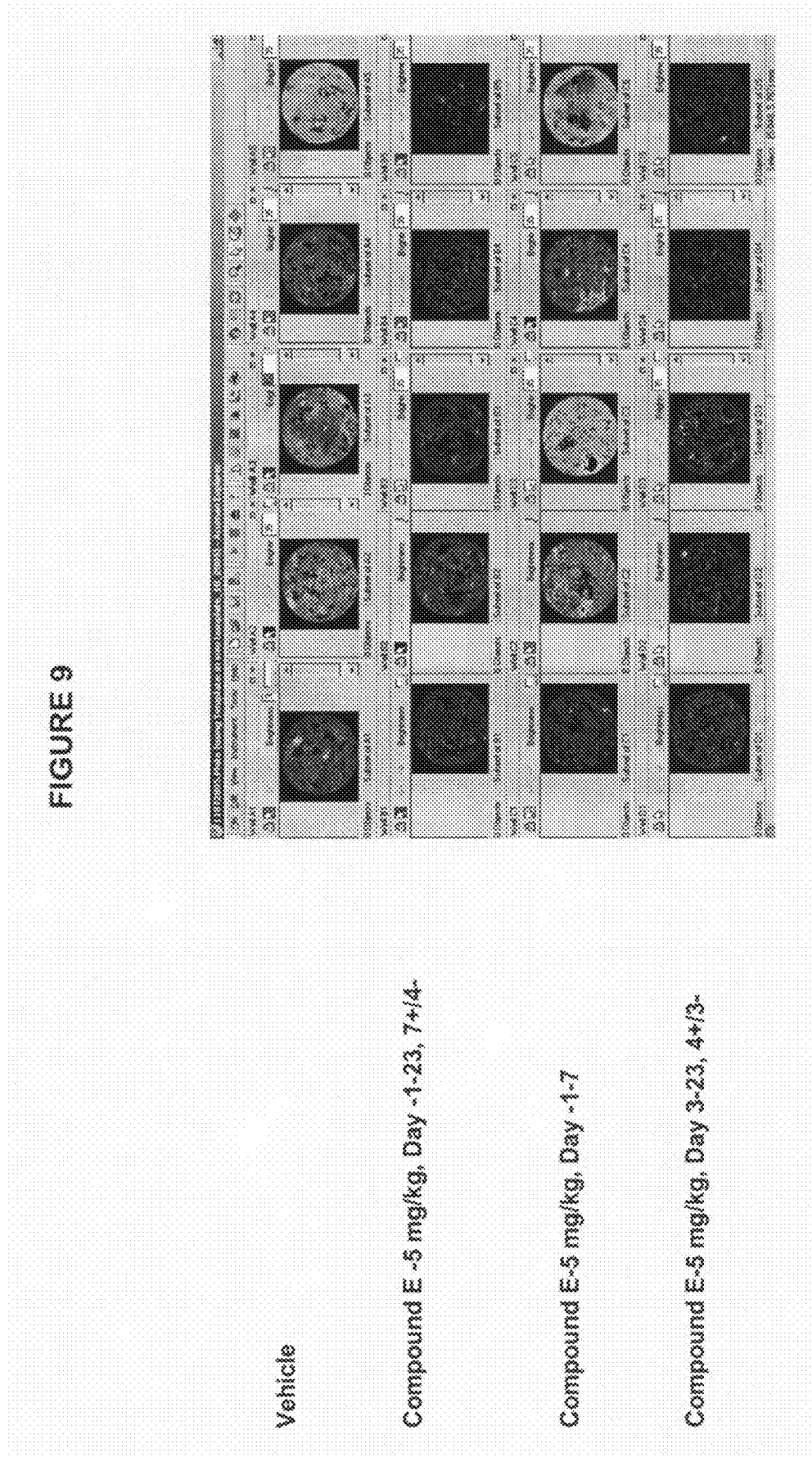
FIG. 9 provides photographs of lung homogenate sample wells of mice treated with 3-methyl-5-(2-chlorophenyl)-7-amino-pyrazolo[3,4][1,4]benzodiazepine (Compound E). Lungs were harvested at day 25 post-implantation ($2 \times 10^6$ cell/mouse iv) and homogenized and determined run on an Acumen Explorer.
Figure 10:
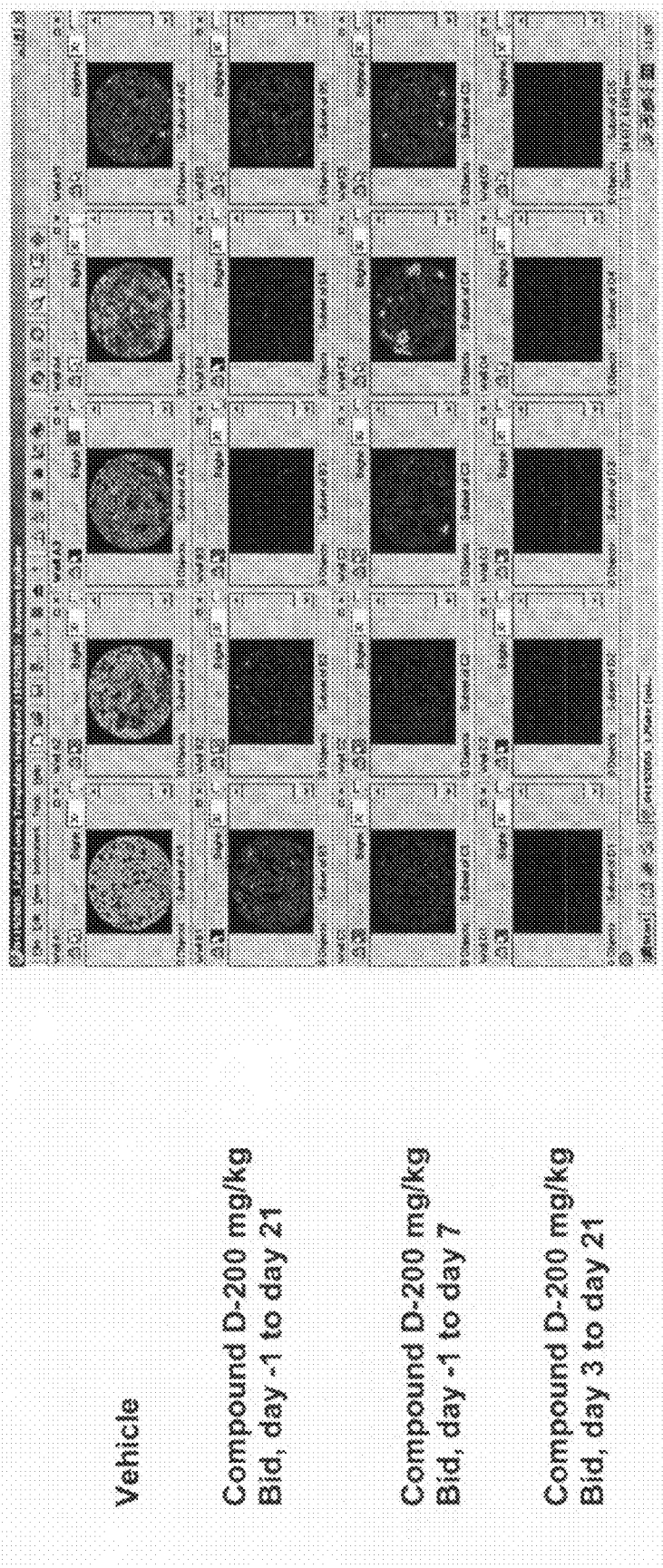
FIG. 10 provides photographs of lung homogenate sample wells of mice treated with 4-[(4S,5R)-4,5-Bis-(4-chloro-phenyl)-2-(2-isopropoxy-4-methoxy-phenyl)-4,5-dihydro-imidazole-1-carbonyl]-piperazin-2-one (Compound D). Lungs were harvested at day 26 post-implantation ($2 \times 10^6$ cell/mouse iv) and homogenized and determined run on an Acumen Explorer.
Figure 11:
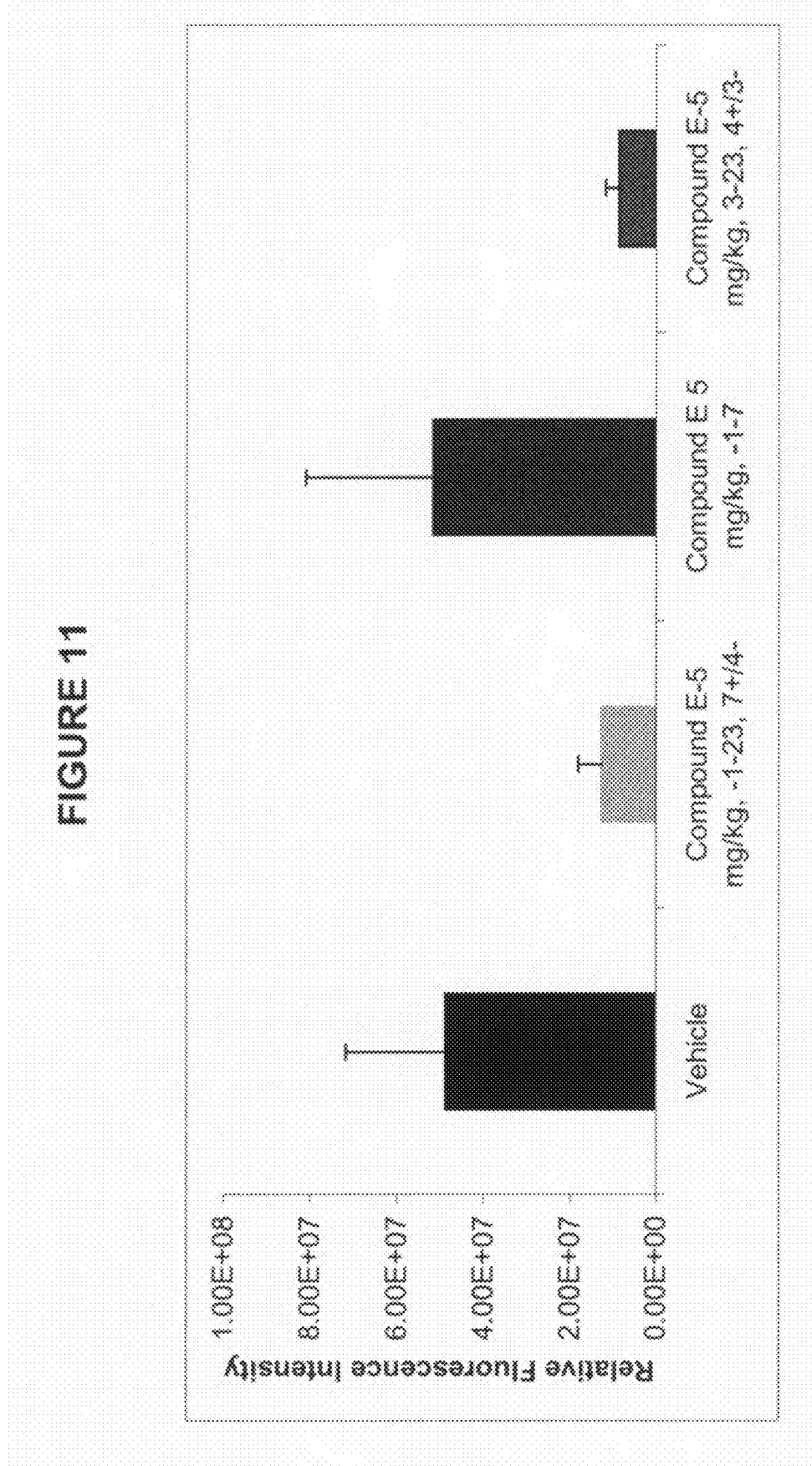
FIG. 11 depicts the relative fluorescence units (RFU) of metastatic lung tissue from SCID beige mice treated with 3-methyl-5-(2-chlorophenyl)-7-amino-pyrazolo[3,4][1,4] benzodiazepine (Compound E) as compared to Vehicle group.
Figure 12:
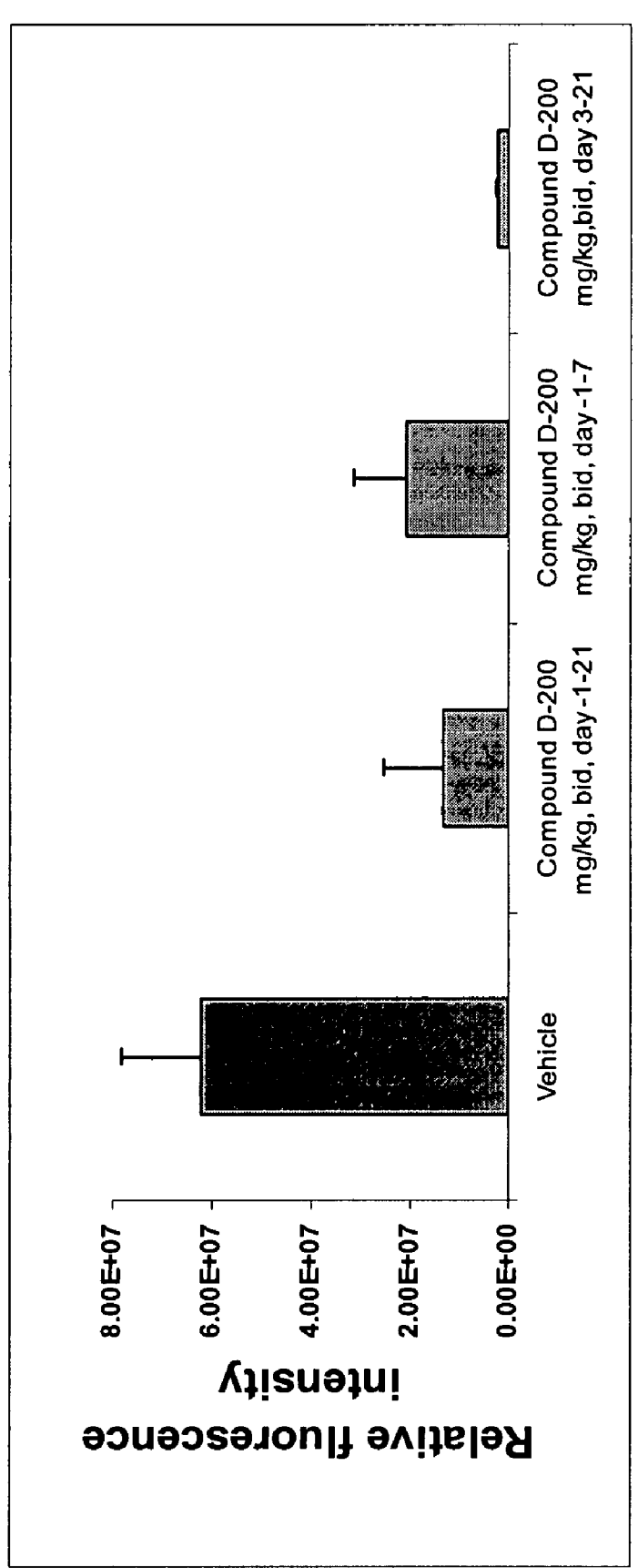
FIG. 12 depicts the relative fluorescence units (RFU) of metastatic lung tissue from SCID beige mice treated with 4-[(4S,5R)-4,5-Bis-(4-chloro-phenyl)-2-(2-isopropoxy-4-methoxy-phenyl)-4,5-dihydro-imidazole-1-carbonyl]-piperazin-2-one (Compound D) as compared to Vehicle group.

Fluorescence Intensity of Lung Homogenates:

5 mice per treatment group were removed from the study at Day 25 or 26 for evaluation of lung metastatic tumor burden. Mice were euthanized, and lungs were removed, placed in 3 ml saline, and homogenized. 0.2 ml of lung homogenate was transferred to a 96 well plate, and fluorescence was read using Acumen Explorer. (FIGS. 9 and 10). Fluorescence was reported in relative fluorescence units (RFU). (Tables 8 and 9, FIGS. 11 and 12). Statistical analysis was determined by Student-test or Mann-Whitney U test, and statistic differences between groups were considered to be significant when the probability value (p) was $\leq 0.05$.

TABLE 8

Relative Fluorescence Units (RFU) of lung homogenate samples run on Acumen Explorer (Compound E Study)

| | | | | P values | | |
|---|---|---|---|---|---|---|
| Treatment | RFU (mean ± SD) | CV | *TGI % At day 25 | Vs Vehicle Group | Vs Day −1-d23 Group | Vs Day −1-d7 Group |
| Vehicle | 48793363 ± 2922819 | 47 | | | | |
| Compound E 5 mg/kg po, bid Day −1-23 | 12738540 ± 5426672 | 43 | 73.9 | 0.022 | | |
| Compound E 5 mg/kg po, bid Day −1-7 | 51670506 ± 29321586 | 57 | −5.9 | 0.87 | 0.040 | |
| Compound E 5 mg/kg po, bid Day 3-23 | 8618508 ± 3198528 | 37 | 82.3 | 0.017 | 0.19 | 0.030 |

*TGI = Tumor growth inhibition relative to Vehicle control group.

TABLE 9

Relative Fluorescence Units (RFU) of lung homogenate samples run on Acumen Explorer (Compound D Study)

| Treatment | RFU (mean ± SD) | CV | *TGI % At day 26 | P value Vs vehicle | P value Vs Day −1-d21 | P value Vs Day −1-d7 |
|---|---|---|---|---|---|---|
| Vehicle | 62091178 ± 16262491 | 26 | | | | |
| Compound D 200 mg/kg po, bid Day −1-21 | 13230372 ± 11960417 | 90 | 78.7 | 0.001 | | |
| Compound D 200 mg/kg po, bid Day −1-7 | 21092887 ± 10460489 | 50 | 66.0 | 0.002 | 0.301 | |
| Compound D 200 mg/kg po, bid Day 3-21 | 2359191 ± 526586 | 22 | 96.2 | 0.001 | 0.077 | 0.004 |

*TGI = Tumor growth inhibition relative to Vehicle control group.

Survival

Figure 13:
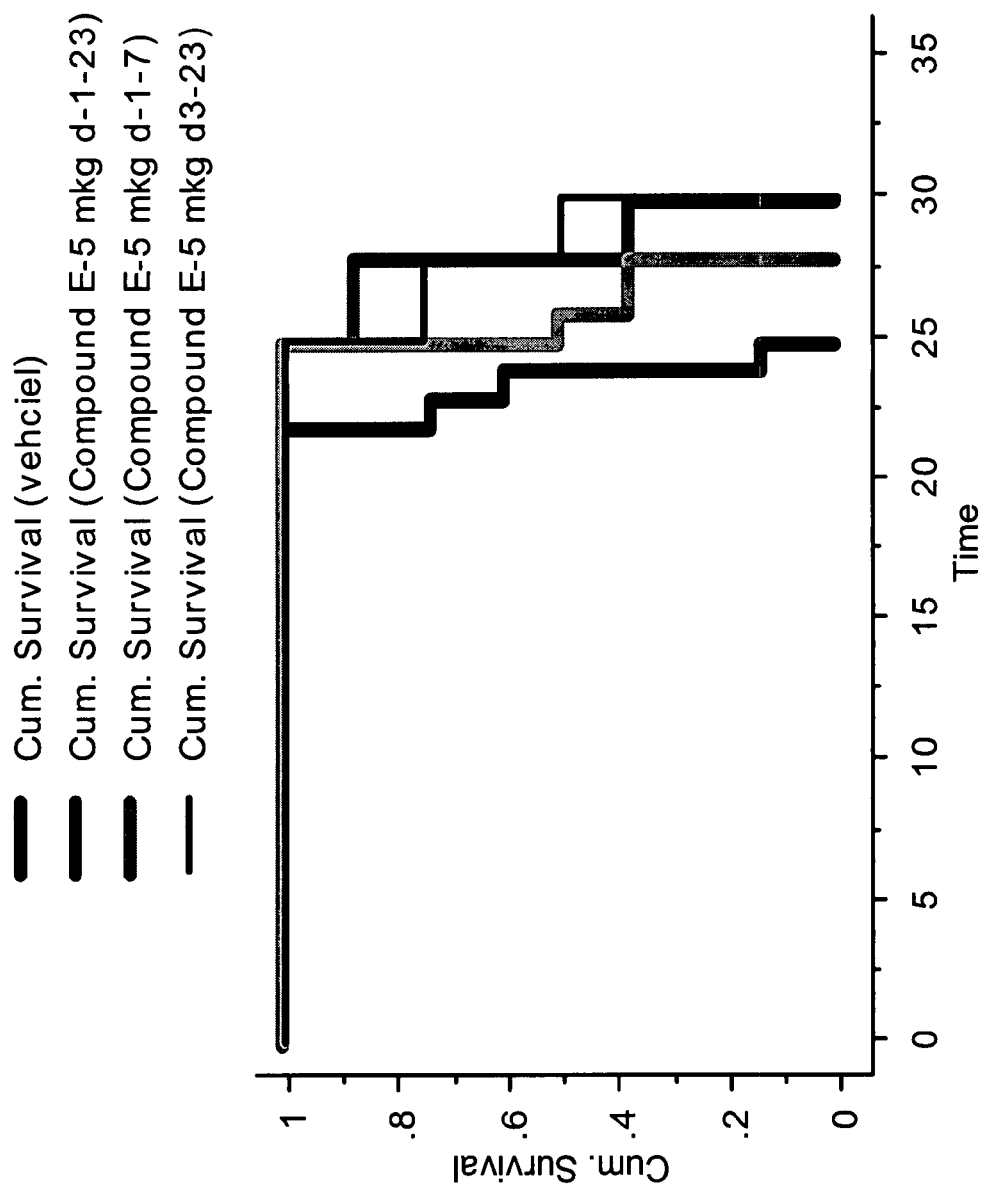
FIG. 13 provides Kaplan-Meier survival curves of SCID beige mice, implanted with LOX-GFP-LM cells, that were treated with 3-methyl-5-(2-chlorophenyl)-7-amino-pyrazolo [3,4][1,4]benzodiazepine (Compound E).
Figure 14:
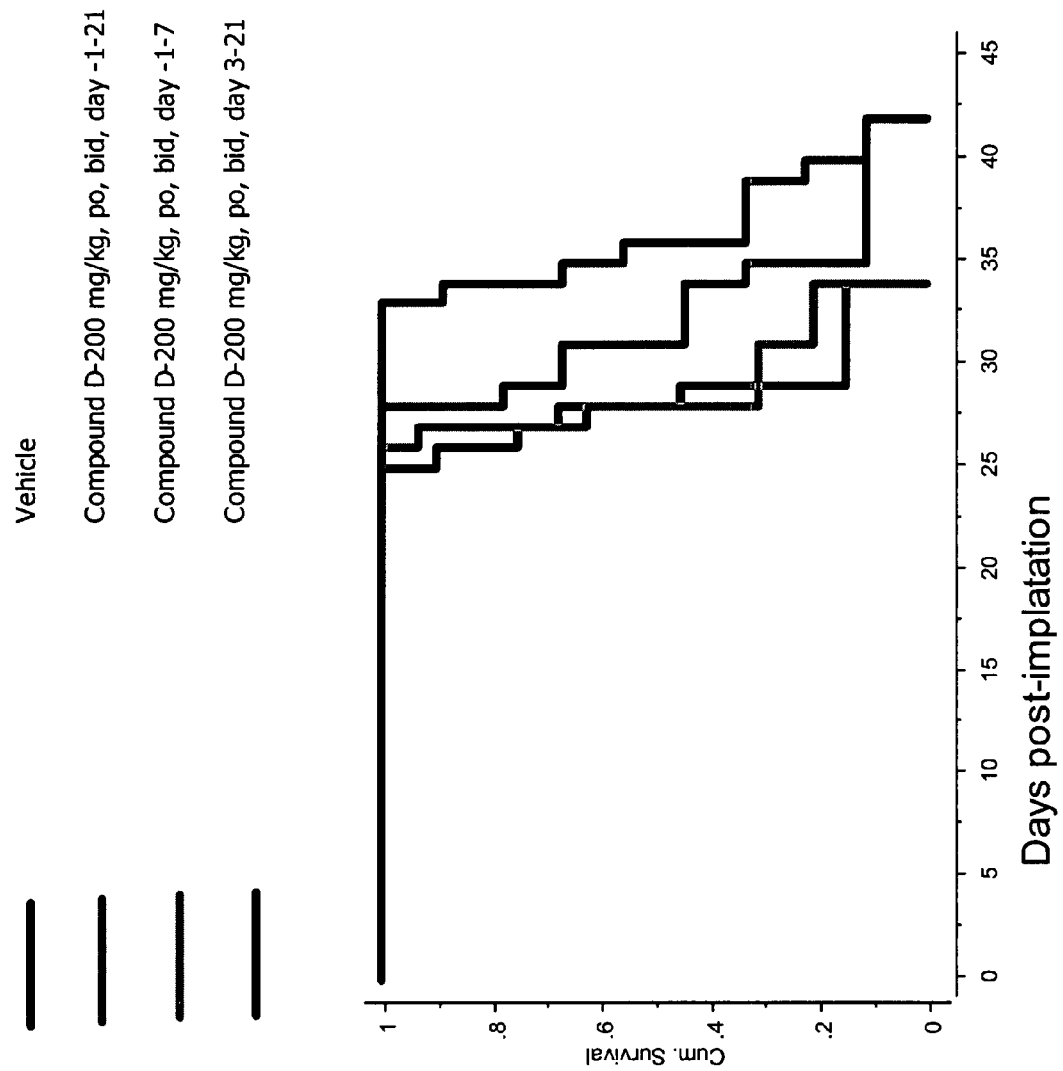
FIG. 14 provides Kaplan-Meier survival curves of SCID beige mice, implanted with LOX-GFP-LM cells, that were treated with 4-[(4S,5R)-4,5-Bis-(4-chloro-phenyl)-2-(2-isopropoxy-4-methoxy-phenyl)-4,5-dihydro-imidazole-1-carbonyl]-piperazin-2-one (Compound D).

Survival represented overall metastatic status either due to lung metastasis or metastasis to other organs. Moribundity due to labored breathing or hind limb paralysis was monitored and recorded as the surrogate endpoint for survival. For survival assessment, results were plotted as the percentage survival against days after tumor implant. The Increased lifetime-span (% ILS) was calculated as: ILS %=100×[(median survival day of treated group−median survival day of control group)/median survival day of control group]. Median survival or (50% survival time) was determined utilizing Kaplan Meier survival analysis. (FIGS. 13 and 14). Differences in survival were analyzed by the log-rank test. Statistic differences between groups were considered to be significant when the probability value (p) was ≦0.05. Similar to the initial characterization of the LOX-GFP-LM metastasis model in Example 5, cells metastasized to lung in 100% of mice when injected iv, and the time frame for observing lung metastasis was also similar (40% survival @ 29 days in the previous study vs. 50% survival @ 24 or 28 days in the present two studies). (Tables 10 and 11; FIGS. 13 and 14)

Compound E had equivalent anti-metastatic activity with either late intervention (Dosed Day 3 through 23) or full length intervention (Day −1 through 23) as assessed by fluorescence intensity of lung homogenates.

Compound D had superior anti-metastatic activity with late intervention (Dosed Day 3 through 23) as compared to Vehicle, as assessed by fluorescence intensity of lung homogenates.

TABLE 10

Survival of groups treated with Compound E as compared to Vehicle control group.

| Treatment | 50% survival days | ILS % | P values Vs Vehicle Group | P values Vs Day −1-d23 | P values Vs Day −1-d7 |
|---|---|---|---|---|---|
| Vehicle | 24 | | | | |
| Compound E 5 mg/kg po, bid Day −1-d23 | 28 | 16.7 | <0.0001 | | |
| Compound E 5 mg/kg po, bid Day −1-d7 | 25 | 4.2 | 0.0001 | 0.02 | |
| Compound E 5 mg/kg po, bid Day 3-d23 | 28 | 16.7 | <0.0001 | 0.83 | 0.03 |

TABLE 11

Survival of groups treated with Compound D as compared to Vehicle control group.

| Treatment | 50% survival days | ILS % | P values Vs Vehicle Group | P values Vs Day −1-d23 | P values Vs Day −1-d7 |
|---|---|---|---|---|---|
| Vehicle | 28 | | | | |
| Compound D 200 mg/kg po, bid Day −1-d21 | 31 | 10.7 | 0.0074 | | |
| Compound D 200 mg/kg po, bid Day −1-d7 | 28 | 0 | 0.649 | 0.03 | |

TABLE 11-continued

Survival of groups treated with Compound D as compared to Vehicle control group.

| Treatment | 50% survival days | ILS % | P values Vs Vehicle Group | Vs Day −1-d23 | Vs Day −1-d7 |
|---|---|---|---|---|---|
| Compound D 200 mg/kg po, bid Day 3-d21 | 36 | 29 | <0.0001 | 0.15 | 0.002 |

Example 10

Comparison of LOX-GFP-LM and LOX-GFP on Experimental Lung Metasis

Previously generated human melanoma LOX-GFP and LOX-GFP-LM cells were maintained in RPMI 1640 medium plus 10% FBS, and 1% Geneticin (G418). Female SCID beige mice (25 mice each tumor line) were injected iv via the tail vein with either the LOX-GFP or LOX-GFP-LM, 2 million cells in a volume of 200 μl serum free RPMI1640. Lungs were harvested from five mice for each time point (day 14, 21 and 28 after implantation, total 15 mice, see Table 12). The rest of the mice, 10 mice per group, were monitored for survival benefit until they were moribund. Two parameters were assessed for quantitative evaluation of tumor growth: 1) fluorescence intensity of lung homogenates and 2) survival.

TABLE 12

Implantation of LOX-GFP and LOX-GFP-LM into SCID beige mice

| Groups | Tumor cell implanted (day 0) | medication | Mice No. | Day of lung harvesting (5 mice/group) |
|---|---|---|---|---|
| 1 | 2 × 10⁶ cell/0.2 ml/ mouse, iv | LOX-GFP-LM | 25 | 14, 21 and 28 |
| 2 | | LOX-GFP | 25 | 14, 21 and 28 |
| Total | | | 50 | |

Figure 18:
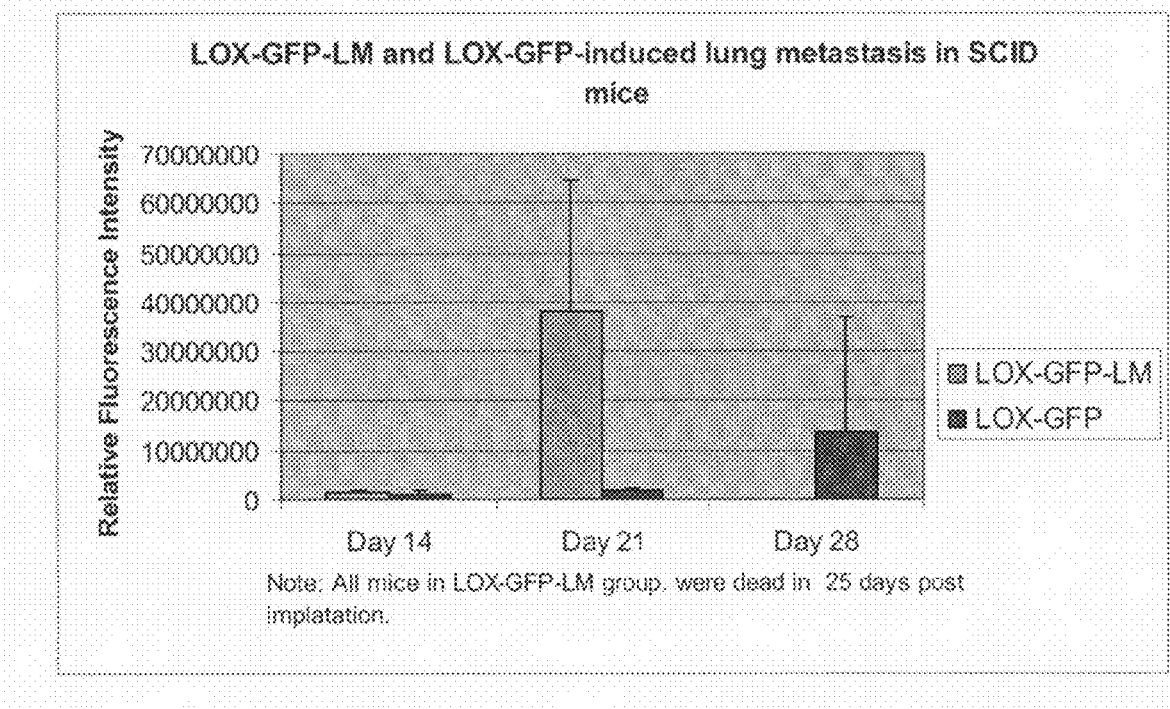
FIG. 18 compares LOX-GFP-LM and LOX-GFP-induced experimental lung metastasis in SCID mice. Samples were measured on a 96 well plate with Acumen Explorer.

Fluorescence Intensity of Lung Homogenates:

Five (5) mice were removed from each group for evaluation of lung metastatic tumor burden. The mice were euthanized, and their lungs were removed, placed in 3 ml saline, and homogenized. Lung homogenate, 0.2 ml, was transferred to a 96 well plate, and fluorescence was read using Acumen Explorer. (FIG. 17). The fluorescence was reported in relative fluorescence units (RFU). (FIG. 18 and Table 13). Statistical analysis was determined by Student-test or Mann-Whitney U test and statistic differences between groups were considered to be significant when the probability value (p) was ≦0.05.

TABLE 13

Summary table of tumor lines (LOX-GFP-LM and LOX-GFP induced experimental metastasis

| Tumor line | Lung metastasis: Relative Fluoresecence Unit (RFU) (mean ± SD) | | | 50% Survival Days |
|---|---|---|---|---|
| | Day 14 | Day 21 | Day 28 | |
| LOX-GFP-LM | 1375463 ± 461906 | 38173338 ± 26458094 | NA | 25 |
| LOX-GFP | 1323534 ± 465272 | 1908836 ± 376654 | 13848195 ± 22888238 | 31 |
| P value | 0.86 | 0.037 | | <0.001 |

Survival Assessment

For survival assessment, moribund mice due to difficulty of breathing or hind limb paralysis as end point were recorded, and results are plotted as percent survival against days after tumor implant. Median survival was determined utilizing Kaplan Meier survival analysis. Differences in survival curves were analyzed by the log-rank test and statistic differences between groups were considered to be significant when the probability value (p) was ≦0.05. (FIG. 19)

Results and Discussion:

SCID beige mice injected with LOX-GFP-LM, as compared to the same strain (SCID beige) of mice injected with LOX-GFP, exhibited a much higher lung metastasis rate (100%) at day 21 and a shorter survival time (all mice were dead in 25 days) with stable GFP transfection in vivo (100%). In the LOX-GFP group, at day 21, two out of five mice were found to have lung metastasis without showing GFP signals, suggesting a lower metastasis rate and non-stable GFP transfection in vivo. 50% survival time in the LOX-GFP group was 6 days delay versus LOX-GFP-LM group (31 days vs 25 days).

Both groups did not show any lung metastasis at day 14. However, in the LOX-GFP-LM group, from day 21 to day 25, the mice either showed strong lung metastasis or were moribund. For the LOX-GFP groups, mice were dead or moribund from day 26 to over day 39. It appeared that there is no plateau time period in terms of tumor burden in lungs; in other words, when the lungs developed extensive lung metastasis, mice will quickly become moribund or dead in a short time period.

CONCLUSION

LOX-GFP-LM causes more lung metastasis with stable GFP signal, as compared to LOX-GFP in the same strain of mice. Both tumor lines showed dynamic tumor burden growth in lungs over time.

The invention claimed is:

1. A method for evaluating a candidate drug or protocol for the treatment of a tumor comprising
   (a) injecting an athymic mouse intraperitoneally with GFP-expressing tumor cells selected from the group consisting of melanoma, breast, prostate, lung, pancreatic, and colorectal cells;
   (b) administering a candidate drug or protocol to said mouse;
   (c) removing ascites for evaluation;
   (f) quantifying the level of GFP in a sample of the ascites using laser-scanning fluoroscopy; and
   (g) comparing the level of GFP in the ascites to that from a control animal which has not been treated with said candidate drug or protocol;
   wherein a decreased level of GFP in the treated sample denotes that the candidate drug or protocol is useful in the treatment of said tumor.

2. The method of claim 1, wherein the tumor cells are LOX, MDA-MB-435, MDA-MB-231, PC-3, DU-145, H460a, A549, MIAPaCa2, HCT116, or HT-29.

3. The method of claim 2 wherein the tumor cells are LOX cells.

4. The method of claim 1, wherein the mouse is a nude mouse.

5. The method of claim 1, wherein the mouse is a SCID beige mouse.

6. The method of claim 1, wherein the GFP-expressing tumor cells contain a neomycin resistant gene.

7. The method of claim 1, wherein the GFP-expressing tumor cells are prepared by
   (a) preparing a vector comprising the nucleic acid encoding a GFP protein;
   (b) transfecting the tumor cells with said vector.

8. The method of claim 7, wherein the vector further comprises the Neo gene for Neo for G418 selection.

9. The method of claim 7, wherein the GFP is from *Renilla mullerei*.

10. The method of claim 1, wherein the GFP is from *Renilla mullerei*.

* * * * *

SEQUENCE LISTING

<160> NUMBER OF SEQ ID NOS: 5

<210> SEQ ID NO 1
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttctaaatac attcaaatat gtatccgctc atgagacaat aaccctgata taggaggtat    60
aaccatg                                                              67

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, c, g, t, unknown or other

<400> SEQUENCE: 2
ggccnnnnng gcc                                                       13

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggccattatg gcc                                                       13

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggccgcctcg gcc                                                       13

<210> SEQ ID NO 5
<211> LENGTH: 4196
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 5
atgcattagt tattaatagt aatcaattac ggggtcatta gttcatagcc catatatgga    60
gttccgcgtt acataactta cggtaaatgg cccgcctggc tgaccgccca acgacccccg   120
cccattgacg tcaataatga cgtatgttcc catagtaacg ccaatagggA ctttccattg   180

-continued

```
acgtcaatgg gtggagtatt tacggtaaac tgcccacttg gcagtacatc aagtgtatca    240
tatgccaagt acgcccccta ttgacgtcaa tgacggtaaa tggcccgcct ggcattatgc    300
ccagtacatg accttatggg actttcctac ttggcagtac atctacgtat tagtcatcgc    360
tattaccatg gtgatgcggt tttggcagta catcaatggg cgtggatagc ggtttgactc    420
acggggattt ccaagtctcc accccattga cgtcaatggg agtttgtttt ggcaccaaaa    480
tcaacgggac tttccaaaat gtcgtaacaa ctccgcccca ttgacgcaaa tgggcggtag    540
gcgtgtacgg tgggaggtct atataagcag agctggttta gtgaaccgtc agatccgcta    600
gcgattacgc caagctcgaa attaaccctc actaaaggga acaaaagctg agctccaca    660 tcggccatta tggccgagca agcagatcct gaagaacacc tgcctgcagg aggtgatgag    720
ctacaaggtg aacctggagg gcatcgttaa caaccacgtg ttcaccatgg agggctgcgg    780
caagggcaac atcctgttcg gcaaccaatt ggtgcagatc cgcgtgacca agggcgcccc    840
cctgcccttc gccttcgaca tcgtgagccc cgccttccag tacggcaacc gtacgttcac    900
caagtacccc aacgacatca gcgactactt catccagagc ttccccgccg gcttcatgta    960
cgagcgcacc ctgcgctacg aggacggcgg cctggtggag atccgcagcg acatcaacct   1020
gatcgaggac aagttcgtgt accgcgtgga gtacaagggc agcaacttcc ccgacgacgg   1080
gcccgtgatg cagaagacca tcctgggcat cgagcccagc ttcgaggcca tgtacatgaa   1140
caacggcgtg ctggtgggcg aggtgatcct ggtgtacaag cttaacagcg gcaagtacta   1200
cagctgccac atgaagaccc tgatgaagag caagggcgtg gtgaaggagt tccccagcta   1260
ccacttcatc cagcaccgcc tcgagaagac ctacgtggag gacggcggct cgtggagca    1320 gcacgagacc gccatcgccc agatgaccag catcggcaag cccctgggat ccctgcacga   1380
gtgggtgtag gccgcctcgg ccgcggccgc atatggcgcg ccgtcgagca tgcatctagg   1440
gcggccaatt ccgcccctct ccctccccc ccctaacgt tactggccga agccgcttgg    1500
aataaggccg gtgtgcgttt gtctatatgt gattttccac catattgccg tcttttggca   1560
atgtgagggc ccggaaacct ggccctgtct tcttgacgag cattcctagg gtctttccc    1620 ctctcgccaa aggaatgcaa ggtctgttga atgtcgtgaa ggaagcagtt cctctggaag   1680
cttcttgaag acaaacaacg tctgtagcga ccctttgcag gcagcggaac cccccacctg   1740
gcgacaggtg cctctgcggc caaaagccac gtgtataaga tacacctgca aaggcggcac   1800
aaccccagtg ccacgttgtg agttggatag ttgtggaaag agtcaaatgg ctctcctcaa   1860
gcgtattcaa caagggctg aaggatgccc agaaggtacc ccattgtatg ggatctgatc    1920
tggggcctcg gtgcacatgc tttacatgtg tttagtcgag gttaaaaaaa cgtctaggcc   1980
ccccgaacca cggggacgtg gttttccttt gaaaaacacg atgataatat ggccacaacc   2040
ttctaaatac attcaaatat gtatccgctc atgagacaat aatattgata taggaggtat   2100
aaatatggga tcggccattg aacaagatgg attgcacgca ggttctccgg ccgcttgggt   2160
ggagaggcta ttcggctatg actgggcaca acagacaatc ggctgctctg atgccgccgt   2220
gttccggctg tcagcgcagg ggcgcccggt tctttttgtc aagaccgacc tgtccggtgc   2280
cctgaatgaa ctgcaagacg aggcagcgcg gctatcgtgg ctggccacga cgggcgttcc   2340
ttgcgcagct gtgctcgacg ttgtcactga agcgggaagg gactggctgc tattgggcga   2400
agtgccgggg caggatctcc tgtcatctca ccttgctcct gccgagaaag tatccatcat   2460
ggctgatgca atgcggcggc tgcatacgct tgatccggct acctgcccat tcgaccacca   2520
agcgaaacat cgcatcgagc gagcacgtac tcggatggaa gccggtcttg tcgatcagga   2580
```

```
tgatctggac gaagaacatc aggggctcgc gccagccgaa ctgttcgcca ggctcaaggc    2640
gagcatgccc gacggcgagg atctcgtcgt gacccatggc gatgcctgct tgccgaatat    2700
catggtggaa aatggccgct tttctggatt catcgactgt ggccggctgg gtgtggcgga    2760
ccgctatcag gacatagcgt tggctacccg tgatattgct gaagaacttg gcggcgaatg    2820
ggctgaccgc ttcctcgtgc tttacggtat cgccgctccc gattcgcagc gcatcgcctt    2880
ctatcgcctt cttgacgagt tcttctgatt cgaagaccga ccaagcgacg cccaacctgc    2940
catcacgaga tttcgattcc accgccgcct tctatgaaag gttgggcttc ggaatcgttt    3000
tccgggacgc cggctggatg atcctccagc gcggggatct catgctggag ttcttcgccc    3060
accctagggg gaggctaact gaaacacgga aggagacaat accggaagga acccgcgcta    3120
tgacggcaat aaaaagacag aataaaacgc acggtgttgg gtcgtttgtt cataaacgcg    3180
gggttcggtc ccagggctgg cactctgtcg ataccccacc gagacccat tggggccaat     3240 acgcccgcgt ttcttccttt tccccacccc acccccaag ttcgggtgaa gcccagggc      3300 tcgcagccaa cgtcggggcg gcaggccctg ccatagcctc aggttactca tatatacttt    3360
agattgattt aaaacttcat ttttaattta aaaggatcta ggtgaagatc cttttttgata   3420 atctcatgac caaaatccct taacgtgagt tttcgttcca ctgagcgtca gaccccgtag    3480
aaaagatcaa aggatcttct tgagatcctt ttttctgcg cgtaatctgc tgcttgcaaa     3540
caaaaaaacc accgctacca gcggtggttt gtttgccgga tcaagagcta ccaactcttt    3600
ttccgaaggt aactggcttc agcagagcgc agataccaaa tactgtcctt ctagtgtagc    3660
cgtagttagg ccaccacttc aagaactctg tagcaccgcc tacatacctc gctctgctaa    3720
tcctgttacc agtggctgct gccagtggcg ataagtcgtg tcttaccggg ttggactcaa    3780
gacgatagtt accggataag gcgcagcggt cgggctgaac gggggggttcg tgcacacagc   3840 ccagcttgga gcgaacgacc tacaccgaac tgagatacct acagcgtgag ctatgagaaa    3900
gcgccacgct tcccgaaggg agaaaggcgg acaggtatcc ggtaagcggc agggtcggaa    3960
caggagagcg cacgagggag cttccagggg gaaacgcctg gtatctttat agtcctgtcg    4020
ggtttcgcca cctctgactt gagcgtcgat ttttgtgatg ctcgtcaggg gggcggagcc    4080 tatgaaaaa cgccagcaac gcggccttt tacggttcct ggccttttgc tggccttttg      4140
ctcacatgtt ctttcctgcg ttatcccctg attctgtgga taaccgtatt accgcc        4196
```